(12) United States Patent
Reynolds

(10) Patent No.: US 10,105,405 B2
(45) Date of Patent: *Oct. 23, 2018

(54) COMPOSITIONS AND METHODS FOR ENHANCING BRAIN FUNCTION USING ACETYL-L-CARNITINE, HUPERZINE A AND GINKGO BILOBA

(71) Applicant: KEYVIEW LABS, INC., Tampa, FL (US)

(72) Inventor: Josh Reynolds, Laguna Beach, CA (US)

(73) Assignee: KeyView Labs, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/337,221

(22) Filed: Oct. 28, 2016

(65) Prior Publication Data

US 2017/0042953 A1    Feb. 16, 2017

Related U.S. Application Data

(63) Continuation-in-part of application No. 15/078,102, filed on Mar. 23, 2016, now Pat. No. 9,737,580, which is a continuation of application No. 14/453,861, filed on Aug. 7, 2014, now Pat. No. 9,308,232, which is a continuation-in-part of application No. 13/307,587, filed on Nov. 30, 2011, now Pat. No. 8,883,814, which is a continuation-in-part of application No. 11/758,151, filed on Jun. 5, 2007, now Pat. No. 8,071,610.

(Continued)

(51) Int. Cl.

| | | |
|---|---|---|
| A01N 43/40 | (2006.01) | |
| A01N 43/42 | (2006.01) | |
| A61K 36/16 | (2006.01) | |
| A61K 31/4748 | (2006.01) | |
| A61K 31/223 | (2006.01) | |
| A61K 9/00 | (2006.01) | |
| A61K 36/185 | (2006.01) | |
| A61K 31/4188 | (2006.01) | |
| A61K 31/381 | (2006.01) | |
| A23L 33/105 | (2016.01) | |
| A23L 33/175 | (2016.01) | |
| A23L 33/15 | (2016.01) | |
| A61K 36/77 | (2006.01) | |
| A61K 36/82 | (2006.01) | |
| A61K 45/06 | (2006.01) | |
| A61K 9/28 | (2006.01) | |
| A61K 31/164 | (2006.01) | |
| A61K 31/197 | (2006.01) | |
| A61K 31/205 | (2006.01) | |
| A61K 31/22 | (2006.01) | |
| A61K 31/221 | (2006.01) | |
| A61K 31/4375 | (2006.01) | |
| A61K 31/4415 | (2006.01) | |
| A61K 31/455 | (2006.01) | |
| A61K 31/473 | (2006.01) | |
| A61K 31/475 | (2006.01) | |
| A61K 31/7028 | (2006.01) | |
| A61K 31/7034 | (2006.01) | |
| A61K 36/41 | (2006.01) | |
| A23L 33/21 | (2016.01) | |

(52) U.S. Cl.

CPC ............ *A61K 36/16* (2013.01); *A23L 33/105* (2016.08); *A23L 33/15* (2016.08); *A23L 33/175* (2016.08); *A23L 33/21* (2016.08); *A61K 9/0053* (2013.01); *A61K 9/28* (2013.01); *A61K 31/164* (2013.01); *A61K 31/197* (2013.01); *A61K 31/205* (2013.01); *A61K 31/22* (2013.01); *A61K 31/221* (2013.01); *A61K 31/223* (2013.01); *A61K 31/381* (2013.01); *A61K 31/4188* (2013.01); *A61K 31/4375* (2013.01); *A61K 31/4415* (2013.01); *A61K 31/455* (2013.01); *A61K 31/473* (2013.01); *A61K 31/475* (2013.01); *A61K 31/4748* (2013.01); *A61K 31/7028* (2013.01); *A61K 31/7034* (2013.01); *A61K 36/185* (2013.01); *A61K 36/41* (2013.01); *A61K 36/77* (2013.01); *A61K 36/82* (2013.01); *A61K 45/06* (2013.01); *A23V 2002/00* (2013.01)

(58) Field of Classification Search

USPC .................................................. 514/277, 290

See application file for complete search history.

(56) References Cited

U.S. PATENT DOCUMENTS 4,775,536 A    10/1988  Patell
4,812,447 A     3/1989  Roberts
(Continued)

FOREIGN PATENT DOCUMENTS

WO         99/51097        10/1999

OTHER PUBLICATIONS

Kennedy et al., "The Dose-Dependent Cognitive Effects of Acute Administration of Ginkgo Biloba to Healthy Young Volunteers," Psychopharmacology (2000); 151:416-423.

(Continued)

*Primary Examiner* — Layla Soroush

(74) *Attorney, Agent, or Firm* — Allen, Dyer, Doppelt + Gilchrist, P.A.

(57) ABSTRACT

A nutritional supplement composition is formulated for oral administration and enhances cognitive function. It includes huperzine A, Ginkgo biloba, and acetyl-L-carnitine. The huperzine A, acetyl-L-carnitine, and Ginkgo biloba together account for at least 80 wt % of a dosage unit of the composition. The Ginkgo biloba is about 5.0% to about 12.0%, by weight of the huperzine A, acetyl-L-carnitine and Ginkgo biloba. The Ginkgo biloba and acetyl-L-carnitine are in a ratio of y:z respectively, wherein y is between about 690 and 1,030 for Ginkgo biloba and z is between about 8,000 and 12,000 for acetyl-L-carnitine.

26 Claims, 5 Drawing Sheets

Related U.S. Application Data

(60) Provisional application No. 60/803,943, filed on Jun. 5, 2006, provisional application No. 60/820,201, filed on Jul. 24, 2006.

(56) References Cited

U.S. PATENT DOCUMENTS

| | | | |
|---|---|---|---|
| 5,104,880 | A | 4/1992 | Kozikowski |
| 5,221,668 | A | 6/1993 | Henningfield et al. |
| 5,668,117 | A | 9/1997 | Shapiro |
| 5,716,614 | A | 2/1998 | Katz |
| 5,911,581 | A | 6/1999 | Reynolds et al. |
| 5,977,162 | A | 11/1999 | Seidman |
| 6,020,139 | A | 2/2000 | Schwartz et al. |
| 6,063,820 | A | 5/2000 | Cavazza |
| 6,117,872 | A | 9/2000 | Maxwell et al. |
| 6,132,727 | A | 10/2000 | Rohde, Jr. et al. |
| 6,335,361 | B1 | 1/2002 | Hamilton |
| 6,435,878 | B1 | 8/2002 | Reynolds et al. |
| 6,479,069 | B1 | 11/2002 | Hamilton |
| 6,562,869 | B1 | 5/2003 | Hamilton et al. |
| 6,773,729 | B2 | 8/2004 | Petrini et al. |
| 6,964,969 | B2 | 11/2005 | McCleary |
| 7,030,154 | B2 | 4/2006 | Ames |
| 8,071,610 | B2 | 12/2011 | Reynolds |
| 8,883,814 | B2 | 11/2014 | Reynolds |
| 9,308,232 | B2 | 4/2016 | Reynolds |
| 9,327,002 | B2 | 5/2016 | Reynolds |
| 9,498,469 | B2 | 11/2016 | Reynolds |
| 2005/0053904 | A1 | 3/2005 | Shephard et al. |
| 2006/0014773 | A1 | 1/2006 | McCleary |
| 2006/0211721 | A1 | 9/2006 | Roberts |
| 2012/0136220 | A1 | 5/2012 | Reynolds |
| 2014/0335191 | A1 | 11/2014 | Reynolds |
| 2014/0348883 | A1 | 11/2014 | Reynolds |
| 2015/0017243 | A1 | 1/2015 | Reynolds |
| 2016/0199432 | A1 | 7/2016 | Reynolds |

OTHER PUBLICATIONS

Allain et al., "Effect of Two Doses of Ginkgo Biloba Extract (EGb 761) on the Dual-Coding Test in Elderly Subjects," Clinical Therapy, May-Jun. 1993; 15(3): 549-558; Abstract Only.
Gold et al., "Ginkgo Biloba: A Cognitive Enhancer?" Psychological Science in the Public Interest; American Psychological Society; vol. 3, No. 1; May 2002; pp. 2-11.
Crews et al., "The Neuropsychological Efficacy of Ginkgo Preparations in Healthy and Cognitively Intact Adults: A Comprehensive Review," The Journal of the American Botanical Council; Herbal Gram; 2005; Issue: 67; pp. 43-62.
Popa, Andreea, "Ginkgo Biloba and Memory," Cleveland Clinic, Center for Continuing Education; Pharmacotherapy Update; vol. V, No. V; Sep./Oct. 2002; 4 pages.
Hagen et al., "Feeding Acetyl-L-Carnitine and Lipoic Acid to Old Rats Significantly Improves Metabolic Function While Decreasing Oxidative Stress," PNAS, vol. 99, No. 4, Feb. 19, 2002, pp. 1870-1875.
Stough et al., "Improving General Intelligence With a Nutrient-Based Pharmacological Intervention," Brain Sciences Institute, Swinburne University, Hawthorn, Victoria, Australia, Intelligence 39, Mar. 2011, pp. 100-107.
Reynolds et al., "Retarding Cognitive Decline With Science-Based Nutraceuticals," Journal of American Nutraceutical Association (JANA), vol. 11, No. 1, 2008, pp. 19-27.
Stough et al., "A Randomized, Double-Blind, Placebo Controlled Study Examining the Effects of a Combination Nutraceutical Formula on Cognitive Functioning and Mood," Journal of the American Nutraceutical Association (JANA), vol. 12, No. 1, 2009, pp. 12-19.
Medina, Alexandre, "Vinpocetine as a Potent Antiintflammatory Agent," PNAS, Jun. 1, 2010, vol. 107, No. 22, pp. 9921-9922.
Jeon et al., "Vinpocetine Inhibits NF-kB-Dependent Inflammation via an IKK-Dependent but PDE-Independent Mechanism," PNAS, May 25, 2010, vol. 107, No. 21, pp. 9795-9800.
Shayne Gad "Pharmaceutical Manufacturing Handbook" (1995, pp. 246, 886, 893-994).
Kiesewetter et al. "Hemorrheological and circulatory effects on Gincosan" Int. j. Clin. Pharmacol. Ther. Toxicol. 192; mar; 30(3): 97-102.
Andres Deluna "The effects of gingko biloba on learning and memory" http://www.medsch.ucla.edu/som/ddo/biolchem/nut-1998/notev3n1/v3n1deluna.html.
Wesnes, et al. "The cognitive, subjective, and physical effects of a ginkgo biloba/panax ginseng combination in healthy volunteers with neurasthenic complaints" Psychopharmacol. bull. 10997; 33(4): 677-83. Abstract Only.
U.S. Appl. No. 15/337,280, filed Oct. 28, 2016.

THE CDR (COGNITIVE DRUG RESEARCH) COMPUTERIZED COGNITIVE ASSESSMENT SYSTEM (AREAS OF COGNITION MEASURED)

LEVEL I: ATTENTION
  THE ABILITY TO SELECT, EVALUATE AND RESPOND TO APPROPRIATE ENVIRONMENTAL INFORMATION

| TASK | COGNITIVE STATES AND PROCESSES ASSESSED |
|---|---|
| SIMPLE REACTION TIME | ALERTNESS, POWER OF CONCENTRATION<br>PRIMARY STAGE OF INFORMATION PROCESSING |
| CHOICE REACTION TIME | AS ABOVE, PLUS STIMULUS DISCRIMINATION; RESPONSE ORGANIZATION |
| DIGIT VIGILANCE | INTENSIVE VIGILANCE; SUSTAINED ATTENTION; ABILITY TO IGNORE DISTRACTION |

LEVEL II: SHORT TERM OR WORKING MEMORY
  THE ABILITY TO TEMPORARILY STORE THE INFORMATION RELEVANT TO ONGOING TASKS

| TASK | COGNITIVE STATES AND PROCESSES ASSESSED |
|---|---|
| NUMERIC WORKING MEMORY | SUB-VOCAL REHEARSAL OF DIGIT SEQUENCES<br>ARTICULATORY LOOP SUB-SYSTEM OF WORKING MEMORY |
| SPATIAL WORKING MEMORY | ABILITY TO TEMPORARILY RETAIN SPATIAL INFORMATION<br>VISUO-SPATIAL SUB-LOOP OF WORKING MEMORY |

LEVEL III: LONG TERM OR EPISODIC SECONDARY MEMORY
  THE ABILITY TO REGISTER, STORE AND RETRIEVE INFORMATION OVER ANY PERIOD REQUIRED

| TASK | COGNITIVE STATES AND PROCESSES ASSESSED |
|---|---|
| WORD RECALL* | ABILITY TO STORE AND RECALL VERBAL INFORMATION; CAPACITY FOR UN-CUED RETRIEVAL OF WORDS; EPISODIC SECONDARY VERBAL RECALL |
| WORD RECOGNITION | ABILITY (SPEED AND SENSITIVITY) TO DISCRIMINATE NOVEL FROM PREVIOUSLY PRESENTED WORDS; EPISODIC SECONDARY RECOGNITION |
| PICTURE RECOGNITION | ABILITY TO DISCRIMINATE NOVEL FROM PREVIOUSLY PRESENTED PICTORIAL INFORMATION; EPISODIC SECONDARY NON-VERBAL VISUAL RECOGNITION |
| FACE RECOGNITION* | ABILITY TO DISCRIMINATE NOVEL FROM PREVIOULY PRESENTED FACES; EPISODIC SECONDARY FACE RECOGNITION |

*FACE RECOGNITION TASK AND WORD RECALL TASK WERE NOT ADMINISTERED IN THIS STUDY.

*FIG. 1*

MEANS AND SDs FOR SIGNIFICANT OUTCOME VARIABLES AT BASELINE AND AGAIN AT 30 DAYS FOR THE COMBINATION NUTRACEUTICAL FORMULA (ProceraAVH) AND PLACEBO GROUPS.

|  | CONDITION | MEAN | Std. DEVIATION | P |
|---|---|---|---|---|
| NUMERIC WORKING MEMORY ORIGINAL STIMULI - ACCURACY - BASELINE | PROCERA AVH | 93.76 | 5.14 | P < .03 |
|  | PLACEBO | 95.77 | 5.26 |  |
| NUMERIC WORKING MEMORY ORIGINAL STIMULI - ACCURACY - WEEK 4 | PROCERA AVH | 95.43 | 3.39 |  |
|  | PLACEBO | 95.03 | 3.94 |  |
| WORD RECOGNITION ORIGINAL STIMULI - SPEED: MEAN - BASELINE | PROCERA AVH | 853.12 | 184.99 | P < .02 |
|  | PLACEBO | 774.99 | 122.44 |  |
| WORD RECOGNITION ORIGINAL STIMULI - SPEED: MEAN - WEEK 4 | PROCERA AVH | 757.52 | 138.40 |  |
|  | PLACEBO | 750.54 | 7.03 |  |
| DEPRESSION/DEJECTION BASELINE (POMS) | PROCERA AVH | 8.00 | 9.42 | P < .06 |
|  | PLACEBO | 5.19 | 8.54 |  |
| DEPRESSION/DEJECTION - WEEK 4 (POMS) | PROCERA AVH | 4.32 | 5.12 |  |
|  | PLACEBO | 4.35 | 6.57 |  |
| ANGER/HOSTILITY BASELINE (POMS) | PROCERA AVH | 7.83 | 7.56 | P < .03 |
|  | PLACEBO | 4.48 | 5.80 |  |
| ANGER/HOSTILITY - WEEK 4 (POMS) | PROCERA AVH | 4.16 | 4.30 |  |
|  | PLACEBO | 3.80 | 6.12 |  |
| TOTAL MOOD DISTURBANCE SCORE BL (POMS) | PROCERA AVH | 65.93 | 30.50 | P < .02 |
|  | PLACEBO | 52.90 | 23.86 |  |
| TOTAL MOOD DISTURBANCE SCORE - WEEK 4 (POMS) | PROCERA AVH | 47.55 | 17.16 |  |
|  | PLACEBO | 46.51 | 21.42 |  |

FIG. 2

COMPOSITIONS AND METHODS FOR ENHANCING BRAIN FUNCTION USING ACETYL-L-CARNITINE, HUPERZINE A AND GINKGO BILOBA

RELATED APPLICATION(S)

This is a continuation-in-part of U.S. application Ser. No. 15/078,102 filed Mar. 23, 2016, which is a continuation of U.S. application Ser. No. 14/453,861 filed Aug. 7, 2014 (now U.S. Pat. No. 9,308,232), which is a continuation-in-part of U.S. application Ser. No. 13/307,587 filed Nov. 30, 2011 (now U.S. Pat. No. 8,883,814), which is a continuation-in-part of U.S. application Ser. No. 11/758,151, filed Jun. 5, 2007 (now U.S. Pat. No. 8,071,610), which claims priority to U.S. provisional application Ser. No. 60/803,943, filed Jun. 5, 2006, and U.S. provisional application Ser. No. 60/820,201, filed Jul. 24, 2006, the disclosures which are incorporated by reference herein.

FIELD OF THE INVENTION

The field of the invention is nutritional supplements and methods therefore, especially as they relate to enhancers of cognition and mood.

BACKGROUND OF THE INVENTION

There are numerous approaches known in the art to enhance mood and cognitive performance in normal individuals, including pharmaceutical interventions, aerobic exercise and certain cognitive training programs. Recently, certain nutraceutical agents, such as, *ginkgo biloba*, and multi-agent compounds have claimed cognitive enhancing effects. Unfortunately, most of those agents and compounds make claims based on mere inclusion of one or more individual ingredients whose clinically demonstrated efficacy level(s), or minimal therapeutic threshold amount(s), are typically not achieved in the proposed multi-agent compound.

In other examples, various supplements and formulations comprising a multiplicity of allegedly active ingredients are marketed as nootropics, or cognitive enhancing agents. For example, the commercially available "Focus Factor" formulation sports over 30 ingredients, while the commercially available "Brain Lightning" formulation has nearly 20 ingredients. Other formulations have been available recently. Such formulations as marketed include multiple active ingredients with respective specific effects, and therefore, often suggest that multiple active ingredients will provide additive, or even synergistic beneficial effects. There have been some clinical trails on some of these other formulations and some improvements seen, but results have been mixed. Indeed, the beneficial effects of selected ingredients, which individually show cognitive benefits, but when combined may possibly even be canceled out by sensory or metabolic overstimulation. For instance, overstimulation of the cholinergic neurotransmitter system is known to cause receptor desensitization and downregulation of density.

Moreover, the few isolated compounds claiming one or more cognitive effects that have been subjected to well controlled (e.g., randomized, double blind, placebo controlled) clinical trials in relatively significant sample sizes (e.g., >50) have only shown clinical effect in selected populations (e.g., an older population, cognitively impaired, abnormal, or low normal subpopulation), and may therefore have no significant effect in a healthy population of relatively wide age range. For example, certain conditions of compromised cognitive and mood function (e.g., chronic stress, sleep loss, depression, poor diet, aging) can be individually treated by targeting and addressing the underlying neuro-chemical imbalance(s). For instance, a lack of certain B vitamins, such as, B-1 or B-12, or minerals, such as, magnesium or selenium, can induce low normal to impaired states of cognition. Such nutritional supplementation can often restore partial or full cognitive functioning. In one example, Oakland intercity kids with extremely low IQ status, were given a cocktail of certain vitamins and minerals and showed an increase of over 10% in IQ points. In general, however, there have been few if any qualified studies showing single or multi-agent compounds positively and significantly effecting mood and cognitive status in a healthy, broad age range population.

Therefore, while numerous compositions and methods for cognitive enhancement are known in the art, all or almost all of them suffer from one or more disadvantages. Thus, there is still a need to provide improved nootropic compositions and methods, for improvements in mood and cognitive function in both abnormal, low normal and normal high functioning general population groups.

SUMMARY OF THE INVENTION

The present invention is directed to compositions and methods of enhancing mood and cognitive function in a human, and particularly to orally administered compositions. Especially preferred compositions have been clinically proven to increase selected aspects of mood and cognition and comprise a minimum number of active ingredients near, at or above their proven therapeutic threshold. As noted in the parent application Ser. No. 15/078,102 filed Mar. 23, 2016, and grandparent application as now issued U.S. Pat. No. 9,308,732, the inventor had found it was possible to use *Ginkgo biloba* to substitute for vinpocetine. Details concerning the ratios and concentration ranges are set forth.

A nutritional supplement composition enhances cognitive function and comprises huperzine A, *Ginkgo biloba*, and acetyl-L-carnitine. The composition is formulated for oral administration such that the huperzine A, acetyl-L-carnitine, and *Ginkgo biloba* together account for at least 80 wt % of a dosage unit of the composition and the *Ginkgo biloba* is about 5.0% to about 12.0% by weight of the huperzine A, acetyl-L-carnitine and *Ginkgo biloba*. The *Ginkgo biloba* and acetyl-L-carnitine are in a ratio of y:z respectively, wherein y is between about 690 and 1,030 for *Ginkgo biloba* and z is between about 8,000 and 12,000 for acetyl-L-carnitine.

The huperzine A, *Ginkgo biloba*, and acetyl-L-carnitine may be in a ratio of x:y:z, respectively, wherein x is between about 0.85 and about 1.3 for huperzine A, y is between about 690 and about 1,030 for *Ginkgo biloba*, and z is between about 8,000 and about 12,000 for acetyl-L-carnitine. In another example, x is between about 0.95 and about 1.20 for huperzine A, y is between about 775 and about 945 for *Ginkgo biloba*, and z is between about 9,000 and about 11,000 for acetyl-L-carnitine. The acetyl-L-carnitine may be present in an amount from about 1,160 mg to about 1,860 mg. The *Ginkgo biloba* may be present in an amount from about 100 mg to about 160 mg. The huperzine A may be present in an amount from about 50 mcg to about 200 mcg.

In another example, the composition is formulated with an enteric coating and may comprise an inactive ingredient selected from the group consisting of a carrier, a binder, an excipient, a dye, and combinations thereof. The huperzine A, *Ginkgo biloba*, and acetyl-L-carnitine together may account for at least 90 wt % of a dosage unit of the composition, and in another example, the huperzine A, *Ginkgo biloba*, and acetyl-L-carnitine together may account for at least 95 wt % of the dosage unit of the composition. In yet another example, the dosage unit of the composition is equal or less than about 1,500 mg.

A nutritional supplement composition for enhancing cognitive function comprises huperzine A, *rhodiola*, Ginkgo biloba, acetyl-L-carnitine, biotin, and alpha lipoic acid. The composition is formulated for oral administration such that the huperzine A, *rhodiola, Ginkgo biloba*, acetyl-L-carnitine, biotin, and alpha lipoic acid together account for at least 80 wt % of a dosage unit of the composition. The *Ginkgo biloba* is about 3.5% to about 8.5% by weight of the huperzine A, *rhodiola, Ginkgo biloba*, acetyl-L-carnitine, biotin and alpha lipoic acid, and the alpha lipoic acid is about 11.0 to about 26.0 percent by weight of the huperzine A, *rhodiola, Ginkgo biloba*, acetyl-L-carnitine biotin and alpha lipoic acid. The *Ginkgo biloba* and acetyl-L-carnitine are in a ratio of y:z respectively, wherein y is between about 690 and 1,030 for *Ginkgo biloba* and z is between about 8,000 and 12,000 for acetyl-L-carnitine.

The acetyl-L-carnitine may be present in an amount from about 1,160 mg to about 1,860 mg. The *rhodiola* may be present in an amount from about 250 mg to about 350 mg. The huperzine A may be present in an amount from about 50 mcg to about 200 mcg. The *Ginkgo biloba* may be present in an amount from about 100 mg to about 160 mg. The alpha lipoic acid may be present in an amount from about 300 mg to about 500 mg. The biotin may be present in an amount from about 400 mcg to about 600 mcg. The dosage unit of the composition may be equal or less than about 1,500 mg.

A method for enhancing cognitive function in a person comprises administering a nutritional supplement composition that includes huperzine A, *Ginkgo biloba*, and acetyl-L-carnitine, wherein the *Ginkgo biloba* and acetyl-L-carnitine are in a ratio of y:z respectively, wherein y is between about 690 and 1,030 for *Ginkgo biloba* and z is between about 8,000 and 12,000 for acetyl-L-carnitine. The method further comprises formulating the nutritional supplement composition for oral administration such that huperzine A, acetyl-L-carnitine, and *Ginkgo biloba* together account for at least 80 wt % of a dosage unit of the composition.

The method may comprise formulating the nutritional supplement composition such that the *Ginkgo biloba* is about 5.0% to about 12.0% by weight of the huperzine A, acetyl-L-carnitine and *Ginkgo biloba*. The huperzine A, *Ginkgo biloba*, and acetyl L-carnitine may be in a ratio of x:y:z, respectively, wherein x is between about 0.85 and about 1.3 for huperzine A, y is between about 690 and about 1,030 for *Ginkgo biloba*, and z is between about 8,000 and about 12,000 for acetyl-L-carnitine. X may be between about 0.95 and about 1.20 for huperzine A, y is between about 775 and about 945 for *Ginkgo biloba*, and z is between about 9,000 and about 11,000 for acetyl-L-carnitine. The acetyl-L-carnitine is present in an amount from about 1,160 mg to about 1,860 mg. The *Ginkgo biloba* is present in an amount from about 100 mg to about 160 mg. The huperzine A may be present in an amount from about 50 mcg to about 200 mcg. The composition may be formulated with an enteric coating. An inactive ingredient may be selected from the group consisting of a carrier, a binder, an excipient, a dye, and combinations thereof. The huperzine A, *Ginkgo biloba*, and acetyl-L-carnitine together may account for at least 95 wt % of the dosage unit of the composition. The dosage unit of the composition may be equal to or less than about 1,500 mg.

The method further comprises adding *rhodiola*, biotin and alpha lipoic acid and formulating the nutritional supplement composition for oral administration such that huperzine A, *rhodiola, Ginkgo biloba*, acetyl-L-carnitine, biotin, and alpha lipoic acid together account for at least 80 wt % of a dosage unit of the composition and the *Ginkgo biloba* is about 3.5% to about 8.5% by weight of the huperzine A, *rhodiola, Ginkgo biloba*, acetyl-L-carnitine, biotin and alpha lipoic acid and the alpha lipoic acid is about 11.0% to about 26.0% by weight of the huperzine A, *rhodiola, Ginkgo biloba*, acetyl-L-carnitine biotin and alpha lipoic acid.

The *rhodiola* may be present in an amount from about 250 mg to about 350 mg. The alpha lipoic acid may be present in an amount from about 300 mg to about 500 mg. The biotin may be present in an amount from about 400 mcg to about 600 mcg. The dosage unit of the composition may be equal or less than about 1,500 mg.

Various objects, features, aspects and advantages of the present invention will become more apparent from the following detailed description of preferred embodiments of the invention.

BRIEF DESCRIPTION OF THE DRAWINGS

Other objects, features and advantages of the present invention will become apparent from the detailed description of the invention which follows, when considered in light of the accompanying drawings in which:

FIG. 1 is a table showing the cognitive tests cited in the more comprehensive report of testing of the Procera AVH composition set forth in the JANA article entitled, "A Randomized, Double-Blind, Placebo Controlled Study Examining the Effects of a Combination Nutraceutical Formula on Cognitive Functioning and Mood," in accordance with a non-limiting example.

FIG. 2 is a table showing the means and standard deviations for significant outcome variables at baseline and again at 30 days for the Procera AVH composition and placebo groups in accordance with a non-limiting example.

DETAILED DESCRIPTION

Figure 3:
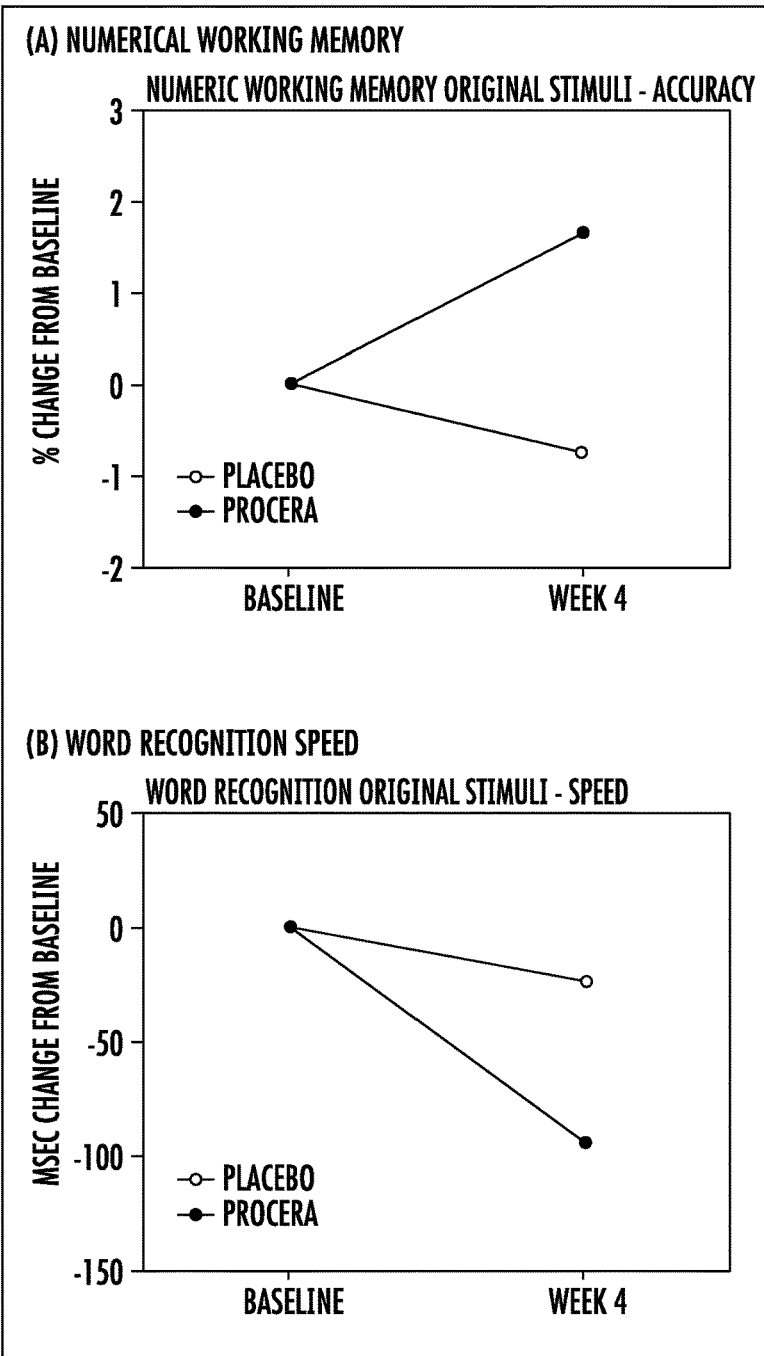
FIG. 3 are graphs showing the numeric working memory accuracy and word recognition speed (long term memory) for the placebo and the Procera AVH composition in accordance with a non-limiting example.

The inventor has discovered that specific combinations of nutritionally safe compounds have significant and desirable effect on cognitive and mood function while having a minimum number of active ingredients at proven minimal therapeutic threshold levels. Moreover, all of the active ingredients in contemplated compositions were selected to impact the largest number of neuro-cognitive structures and functions in the human brain. Furthermore, contemplated compositions are effective for optimal improvement of cognitive states and status ranging from normal to declining more rapidly than normal, or accelerated stages of decline, to pre-dementia states (e.g., MCI-mild cognitive impairment), and even MCI precursor states (e.g., AAMI, or age-associated memory impairment).

It should be particularly appreciated that contemplated formulations are, to the best of the inventor's knowledge, the first formulations that have been administered to a cognitively normal, or healthy, broad age range group and clinically shown to enhance attention (aka focus, concentration) short term working memory, memory consolidation and processing speed, mental clarity and energy, fluid intelligence, general reasoning and executive functions and a broad range of moods (e.g., to reduce depressed states, anxiety, confusion, hostility and anger). Particularly, contemplated compositions have been demonstrated to improve with high statistical significance numerical working memory accuracy (working memory), word recognition speed (long term memory consolidation), anger-hostility (mood), and total mood disturbance (mood).

Contemplated compositions have further substantially improved (to near statistical significance) spatial working memory accuracy (working memory), attention, depression (mood), confusion (mood), and vigor (mood).

In contrast, heretofore known nootropic formulations include a large range of ingredients (e.g., U.S. Pat. No. 6,964,969 listing 47 ingredients) with unknown interactions, wherein clinical information on cognitive enhancement was only available for isolated ingredients. Therefore, and as pointed out in more detail further below, the presumed effect of such formulations was based on a summarization of known effects of individual ingredients, which is in most if not all cases inconsistent with the actual effect. On the other hand, certain supplements have been tested and were found effective in a specific manner (e.g., Eur. J. Pharmacol. 2000; 398(1):56-72 where improvement of cognitive function in rats with chronic cerebral hypoperfusion is reported). As a consequence, these supplements are often marketed with unsubstantiated and/or overextended claims with regard to their alleged effect on human cognition as the reported and specific effects often fail to translate into specific and measured advantages in human.

In one exemplary and preferred formulation, a nutritional supplement or pharmaceutical composition is prepared that includes a therapeutically effective daily dosage of acetyl-L-carnitine (preferably 1,250-2,000 mg/d, and even more preferably 1500 mg/d), vinpocetine (preferably 10-30 mg/d, and even more preferably 15 mg/d) or *rhodiola* extract (also referred to herein as '*rhodiola*', preferably standardized to 3% rosavins and 1% salidroside, and most preferably 250-350 mg, and most preferably about 300 mg), and huperzine A (preferably 50-200 mcg/d, and even more preferably 150 mcg/d). Additionally, such formulations may further include alpha lipoic acid (preferably in an amount of 300-500 mg, most preferably about 400 mg as a daily dosage), *rhodiola* (preferably in an amount of 200-400 mg, most preferably about 300 mg as a daily dosage), and biotin (preferably in an amount of 400-600 mcg, most preferably about 500 mcg as a daily dosage). The following table illustrates exemplary compositions.

|  | Formulation I | Formulation II |
| --- | --- | --- |
| Acetyl-L-carnitine | 1,500 mg | 1,500 mg |
| Vinpocetine | 15 mg (or *rhodiola*) | 15 mg |
| Huperzine A | 150 mcg | 150 mcg |
| Alpha lipoic acid | —/— | 400 mg |
| Biotin | —/— | 500 mcg |
| *Rhodiola* | 300 mg (or vinpocetine) | 300 mg |

Here, Formulation I has as alternative ingredients vinpocetine and *rhodiola*, and based on unpublished considerations and observations, both versions of Formulation I are deemed to be equivalent with respect to the biological effects. Moreover, it is also contemplated that Formula I can include both, vinpocetine and *rhodiola*. Such formulation is expected to have increased benefits in the mood measures in addition to the benefits for Formula I without *rhodiola*. Formulation II is also known as Procera, while Formulation II is also known as Ceretrophin. Experimental data for both Formulations are provided in the experimental section below.

It is also possible to use *gingko biloba* with or in addition to or in substitution of the vinpocetine if vinpocetine is not available commercially. There were past instances when vinpocetine was not readily available commercially, and thus, *rhodiola* could be used as a substitute in Formulation I as a possibility. *Rhodiola* has been known to have pleiotropic properties and have multiple mechanisms of action.

Most preferably, the effective daily dosage is administered between once daily and four times daily in dosage units of accordingly adjusted weight. While not limiting to the inventive subject matter, acetyl-L-carnitine in contemplated formulations is thought to increase cerebral energy metabolism by assisting in mitochondrial beta-oxidation and to donate an acetyl moiety for synthesis of acetylcholine, while Vinpocetine (several other unique mechanisms of action, including anti-inflammatory at microglial level) is thought to dilate blood vessels in the brain, as well as improve red blood cell deformability, to thus allow for better perfusion into and throughout neuro-cognitive regions and structures of the brain. Vinpocetine is known as a potent anti-inflammatory agent and its anti-inflammatory action is believed to be caused by a direct inhibition of the IkB kinase complex (IKK) rather than PDE blockage. It also inhibits subsequent induction of pro-inflammatory mediators and multiple cell types, including vascular smooth muscle cells, endothelial cells, microphages, and epithelial cells. It also inhibits monocyte adhesion and chemotaxis, which are critical processes during inflammation. Further details are found in the articles entitled: "Vinpocetine as a Potent Antiinflammatory Agent," PNAS, Jun. 1, 2010, Vol. 107, No. 22, pages 9921-9922; and "Vinpocetine Inhibits NF-κB-Dependent Inflammation via an IKK-Dependent but PDE-Independent Mechanism," PNAS, May 25, 2010, Vol. 107, No. 21, pages 9795-9800, the disclosures which are hereby incorporated by reference in their entirety.

Huperzine A is thought to act as an acetylcholine esterase inhibitor and antioxidant, as well as other neuroprotective effects including NMDA receptor antagonism and the down-regulation of glutamate induced calcium mobilization and excitotoxiciy. Huperzine A is isolated from the Chinese herb Huperzia serrata and is a potent, highly specific and reversible inhibitor of acetylcholinesterase. It has been found to reverse or attenuate cognitive deficits in a broad range of animal models. Clinical trials in China have demonstrated that Huperzine A significantly relieves memory deficits in aged subjects, patients with benign senescent forgetfulness, Alzheimer's disease (AD) and vascular dementia (VD), with minimal peripheral cholinergic side effects compared with other AChEIs in use. Huperzine A possesses the ability to protect cells against hydrogen peroxide, β-amyloid protein (or peptide), glutamate, ischemia and staurosporine-induced cytotoxicity and apoptosis. These protective effects are related to its ability to attenuate oxidative stress, regulate the expression of apoptotic proteins Bcl-2, Bax, P53 and caspase-3, protect mitochondria, and interfere with APP metabolism. Antagonizing effects on NMDA receptors and potassium currents may contribute to the neuroprotection as well. It is also possible that the non-catalytic function of AChE is involved in neuroprotective effects of Huperzine A. The therapeutic effects of Huperzine A on AD or VD are probably exerted via a multi-target mechanism.

Therefore, and viewed from a different perspective, contemplated nutritional supplements for enhancing cognitive function include (a) huperzine A, (b) one of vinpocetine and *Rhodiola*, and (c) acetyl-L-carnitine, wherein (a) and (b) and (c) are present in a ratio of x:y:z, wherein x is between 0.8 and 1.2, y is between 80 and 120 for vinpocetine and between 1,600 and 2,400 for *rhodiola*, and z is between 8,000 and 12,000. In such methods, the supplements may include the additional ingredients (i) alpha lipoic acid, (ii) *Rhodiola* where (b) is vinpocetine, and (iii) biotin. In another step, the supplement is preferably formulated for oral administration such that the huperzine A, vinpocetine, and acetyl-L-carnitine together account for at least 80 wt % of a dosage unit of the supplement, or such that the additional ingredients (i), (ii), and (iii) and the huperzine A, vinpocetine, and acetyl-L-carnitine together account for at least 80 wt % of a dosage unit of the supplement. Viewed from a different perspective, huperzine A may present in an amount of about 150 mcg, vinpocetine may be present in an amount of about 15 mg or *rhodiola* may be present in an amount of about 300 mg, and/or acetyl-L-carnitine may present in an amount of about 1,500 mg. Additionally, it is typically preferred that the alpha lipoic acid is present in an amount of about 400 mg, *Rhodiola* is present in an amount of about 300 mg where vinpocetine is present, and biotin is present in an amount of about 500 mcg. As used herein, the term "about" in conjunction with a numeral refers to a range of that numeral +/10%, inclusive. Biotin may protect against its known depletion by alpha lipoic acid.

Where desired, optional additional active ingredients may be added, and especially contemplated include folic acid (typically in an amount of at least 0.1 mg per dosage unit, and more preferably at least 1 mg per dosage unit) or potassium (typically in an amount of at least 10 mg per dosage unit, and more preferably at least 100 mg per dosage unit). Furthermore, contemplated supplements may include inactive ingredients, which may help in formulation, disintegration, or other manner. Therefore, suitable inactive ingredients include carriers, binders, excipients, dyes, etc. Oral formulation is typically in form of a liquid or powder, or gel, or a solid form, and most preferably in form of tablet, pill, dragee, capsule, or softgel which may or may not have an enteric coating, such coating allowing for the ingredients to by-pass the upper GI tract where gastro-intestinal disturbances can be problematic for some individuals. Moreover, one or more of the active ingredients may be in slow release formulation to extend release over a period of between 1-24 hours. In less preferred aspects, the supplement may also be formulated as a liquid or a gel, or embedded in a dissolvable film or chewing preparation.

It is further preferred that the supplement is formulated such that the daily dosage unit of the supplement is equal or less than 1,200 mg, more preferably equal or less than 1,600 mg, and even more preferably equal or less 2,000 mg, and most preferably equal or less than 2,400 mg, wherein administration may be between once daily and ten times daily. Therefore, suitable oral single dosage forms may preferably have a weight between 200 mg and 600 mg. Regardless of the actual weight of the single dosage form, it is preferred that the huperzine A, vinpocetine, and acetyl-L-carnitine together account for at least 80 wt %, more preferably at least 85 wt %, even more preferably at least 90 wt %, and most preferably at least 95 wt % of a dosage unit of the supplement, or wherein the additional ingredients (i), (ii), and (iii), and the huperzine A, vinpocetine, and acetyl-L-carnitine together account for at least 80 wt %, more preferably at least 85 wt %, even more preferably at least 90 wt %, and most preferably at least 95 wt % of a dosage unit of the supplement.

With respect to marketing such compositions it is contemplated that the supplement may be associated with an information (e.g., printed, displayed, or audio) stating that the nutritional supplement enhances attention, short term working memory, memory recall capacity and memory recall speed, mental clarity, mental energy, speed of processing, fluid intelligence, and/or mood. Most preferably, such statement is included on a packaging label. Furthermore, contemplated supplements may be provided with an interactive tool (e.g., computer software, link, flash cards, electronic device, etc.) that allows for testing, training, and/or validation of the cognitive enhancement or that allows for validation of efficacy of the supplement and/or proper personal dosing, or titration of the supplement to achieve optimal efficacy.

Consequently, a method of assisting enhancement of cognitive function in a person using a nutritional supplement includes a step of providing contemplated compositions for oral administration under a schedule and protocol effective to improve cognitive function (with respect to the composition of the supplement, the same considerations as described above apply). Most typically, the cognitive function is a function of one or more types of memory including immediate, short term (a/k/a working memory) and long term (aka episodic, delayed) memory including sensory, procedural, verbal, semantic, numeric, visual, spatial and object learning and recall, a function of memory processing speed, consolidation and retrieval, an aspect of mood, a function of attention (aka focus and concentration), a function of fluid intelligence and processing speed, an executive function, e.g., decision making, multi-tasking (aka task shifting, or switching) and general reasoning. As already pointed out above, the supplement may be provided with an interactive tool that allows at least one of validation of efficacy of the supplement and proper personal dosing, or titration of the supplement.

Experiments

Clinical Study Results of Inventive Composition Vs. Comparative Composition

In the following, the composition according to the inventive subject matter is referred to as Procera, while the second composition was termed comparative composition. Most notably, Procera produced significant widespread, global cognitive effects in short term memory, working memory, and longer term memory consolidation and speed of processing measures. What's more, test subjects displayed improvement in a range of mood measures including depression, anxiety, anger and hostility, and exhibited more mental vigor, confidence and clarity.

This first section of experiments and methods and results were initial studies while a more comprehensive set of the tests and results as part of that original test are set forth below also and taken from the article about this clinical trial entitled, "A Randomized, Double-Blind, Placebo Controlled Study Examining the Effects of a Combination Nutraceutical Formula on Cognitive Functioning and Mood," published in the Journal of the American Nutraceutical Association (JANA), Vol. 12, No. 1, 2009, pages 12-19, the disclosure which is hereby incorporated by reference in its entirety.

It should further be appreciated that the study was conducted with cognitively normal male and female subjects ranging in age from 22-66. Producing an overall effect in such a large demographic group is unexpected. Rather, it could be expected that the type of formulation used herein would only show significant improvements in either a slightly to moderately impaired group and an older group (e.g., age 45 plus), where many conditions of aging and lifestyle factors contribute to an accumulated buildup of neurotoxic factors (e.g., free radical induced oxidative stress, heavy metals, cerebral vascular plaques, including beta amyloid plaques implicated in Alzheimer's, reduced cerebral vascular blood flow and glucose metabolism, calcium dyshomeostasis and others).

Procera Composition (Daily Dose in Mg)

| Huperzine A | 0.15 |
| --- | --- |
| Vinpocetine | 15 |
| Acetyl-L-Carnitine | 1500 |

Comparative Composition (Daily Dose in Mg)

| Huperzine A | 0.15 |
| --- | --- |
| Vinpocetine | 20 |
| Acetyl-L-Carnitine | 1000 |
| Pantothenic Acid | 250 |
| DMAE | 300 |
| Thiamin | 100 |
| Niacin (niacinamide) powder | 250 |

As can be seen, the comparative composition employs similar but significantly distinct amounts of huperzine A, vinpocetine, and acetyl-L-carnitine, and further includes four active ingredients known to have certain cognitive effects as isolated compounds, and purported to act synergistically with the cholinergic-enhancing effects of acetyl-1-carnitine and Huperzine A.

Methods

Participant Selection Criteria; Selection criteria includes those: (1) Not currently taking prescription drugs affecting the brain or nervous system (e.g., Modafinil, acetylcholinesterase inhibitors, anti-cholinergics, stimulants, L-dopa, MAO inhibitors, NMDA receptor antagonists, methylphenidate, amphetamine, pseudo-ephedrine, SSRIs and other antidepressant medication); (2) Not currently taking OTC medications affecting the brain (e.g., ephedra based diet pills); (3) Who have not used any supplements within the past 30 days that have an effect on cognitive function, memory, anxiety, depression (e.g. Ginseng, *Gingko*, Vinpocetine, 5HTP, Tryptophan, St. John's Wort, ephedrine (ephedra), alpha GPC, Citicoline, phosphatidylserine, acetyl-L-carnitine, Focus Factor™; (4) Not active Smokers; (5) Not taking the following: anti-coagulant drugs (Warfarin, Heparin, Plavix); anticholinergics or acetylcholinesterase inhibitors (bethanechol (Ureholine), donepezil (Aricept), rivastigmine (Exelon), galantamine (Reminyl), edrophonium (Enoln, Reversol, Tensilon), neostigmine (Prostigmin); (6) Do not have any of the following health conditions: AIDS, HIV; Chronic Fatigue Syndrome, Epstein Barr, Fibromyalgia, Lupus, Multiple Sclerosis, Thyroiditis, Ulcerative Colitis, Crohn's Disease, Irritable Bowel Syndrome, dementia including Alzheimer's and Parkinsons' disease, Type 1 or 2 Diabetes, Insomnia or Sleep Apnea, Narcolepsy; (7) No history of head trauma; (8) No neurological deficits; (9) Not pregnant or lactating; (10) Not anticipating any planned changes in lifestyle (e.g. exercise regimen) for the duration of the study; (11) No known allergies to nuts.

In the initial methodology and results, 90 healthy participants between the ages of 22-66 years of age were tested in treatment and placebo groups (total number of participants is n=100). A drop out rate (voluntary and non-voluntary withdrawal) of approximately 20% was expected and therefore additional participants were recruited for the study. The above-identified and incorporated by reference JANA article sets forth more detailed results from the trial and explains that the combination nutraceutical formula included the huperzine A, vinpocetine, and acetyl-L-carnitine and was examined in a 30-day, double blind, placebo controlled clinical trial and assessed a range of cognitive and mood variables. As noted in the article, seventy-four (74) healthy participants completed the study, with 43 in the combination nutraceutical formula group, and 31 in the placebo group, and a mean age of 48 years. The data from that trial is explained below and provides evidence that the composition proves a range of cognitive and mood variables that were observable using a highly standardized and reliable battery of cognitive tasks. The mood changes were readily observed and reported by the participants. The composition improves functioning during complex cognitive tasks that assess memory such as working and long term or consolidation rather than in simple discrimination tasks such as choice reaction time. The cognitive processes that appear to be improved relate to the various stages of working memory processes including the initial (information) registration (i.e., forming a "memory trace"), the further consolidation of information into memory stores and the later stages of memory retrieval. This may suggest a specific focus of effect on the human brain and incorporating frontal and temporal circuits that underpin working memory and long term memory consolidation and retrieval. Mental clarity and mental energy appear to be improved most likely modulated by increased neurotransmitter function, cerebral metabolism and mitochondrial energetics.

The study as initially set forth was advertised in Melbourne newspapers, on community notice boards, the Brain Sciences Institute website, and via the Brain Sciences to Institute database of interested participants. All interested individuals were screened over the phone by the research nurse to assess their suitability for participation in the study. Subjects participated in periodic evaluation of their cognitive functions including memory, mood, energy and mental status by taking a battery of computerized tests and written questionnaires that assessed their cognitive functions which including attention, memory, executive function, mood, energy, stress level, state of mind and IQ.

The following neuropsychological tests were employed in the currents study:

(1) The Cognitive Drug Research measure (CDR) is a well-validated test, which was used to assess attention, working memory and episodic secondary (longer term memory, or consolidation). (2) Inspection time (IT) is a measure speed of early information processing. (3) The Profile of Mood States (POMS) is a self-report designed to measure six dimensions of mood: tension-anxiety; depression-dejection; anger-hostility; vigor-activity; fatigue-inertia; and confusion-bewilderment. (4) IQ was assessed using the Raven's Progressive Matrices. This was done by administering the even items at baseline and the odd items at Week 4. (5) The UWIST Mood Adjective Checklist was used to measure mood states and energy levels. (6) The Spielberger State-Trait Anxiety Inventory is a 20-item questionnaire, to measure anxiety at the time of testing. (7) Perceived Stress Scale was used to measure stress symptoms and effective coping.

Participants visited Swinburne University on 3 separate occasions 1) Visit 1: Health assessment, practice, baseline and acute testing 2) Visit 2: 1 week (7 days) following baseline testing and 3) Visit 3: 4 weeks (28 days) following baseline testing. During the first visit, participants completed a general health assessment and were then allocated into one of three treatment groups for baseline and acute testing. Timeline for each testing period:

Baseline and Acute Testing

Baseline testing: 1. General health assessment: blood pressure, height, weight; 2. Random allocation of participants into one of the three treatment groups; 3. CDR practice testing which is required in order to become familiar with the tests and what is required of participants; 4. CDR baseline testing; 5. Mood and energy scales will be administered—POMS, STAI, UWIST mood adjective checklist, PSS and Raven's Matrix.

Acute testing: 6. Groups were administered an initial dose of 2 tablets along with a snack of a peanut butter sandwich for adequate absorption of fat-soluble ingredients and minimization of gastric distress from the consumption of acetyl-L-carnitine. 7. 30 mins after initial dose of 2 tablets, a second dose of 2 tablets was administered again with a snack as in step 5. 8. Following 60 minutes after the second dose (90 minutes after initial dose) participants performed CDR testing. Participants were then asked to take the appropriate number of tablets per day for 4 weeks (28 days) according to their assigned treatment group. All participants were asked to visit Swinburne University for a re-test at week 1 and at the completion of the treatment period at week 4. Subjects were given a Symptom Checklist to take home to monitor for any side effects and symptoms that they experience on a weekly basis.

Testing sessions 2 and 3 (1 and 4 weeks following baseline testing; Total time=approx 50 minutes): 1. CDR, Inspection Time and Raven's matrix (week 4 only). 2. Mood and energy scales will be administered—POMS, STAI, UWIST mood. Adjective checklist, PSS; 3. Participants submitted weekly symptom checklist 4. General health assessment.

We used alternate forms of psychometric tests to reduce practice effects as much as possible and to maximize the power of the study. General health assessments were undertaken by the BSI research nurse. Testing sessions were consistent on each testing day. Participants were requested not to have alcohol or caffeine-containing food or beverages on the testing days (e.g., coffee, tea, chocolate and energy drinks containing caffeine or guarana). Further to control for food intake participants they were also required to eat a light breakfast (e.g., 2 pieces of toast or cereal with juice) on the testing days.

Results

Cognitive Measures

Simple Reaction Time: The speed of simple reaction time did not significantly improve due to the Procera treatment across the 4 weeks of administration. This is the simplest cognitive measure in the cognitive battery.

Digit Vigilance and Choice Reaction Time: These measures were excluded from analysis because of the large number of participants who reached 100% accuracy at baseline serving to cause these variables to show a ceiling effect. This effect significantly reduces the variance in measures and invalidates parametric (statistical) testing of differences. Conceptually it is pointless to examine an effect of improvement from baseline to time two if the majority of the sample has already reached perfect performance at baseline.

Spatial Working Memory: There was a trend towards significance for Spatial Working Memory Accuracy (p=0.17). Although not significant, the results (see mean values below) indicate that there was more of an improvement in accuracy over the treatment duration for the Procera than for the placebo. Larger sample size may help this result become statistically significant. This result should be treated as a preliminary finding that should be subjected to replication in a larger sample.

|  | Condition | Mean | Std. Deviation | N |
|---|---|---|---|---|
| Spatial Working Memory New Stimuli-Accuracy-baseline | Procera AVH | 94.7222 | 8.53099 | 36 |
|  | Placebo | 96.6071 | 5.27987 | 28 |
|  | Total | 95.5469 | 7.29847 | 64 |
| Spatial Working Memory New Stimuli-Accuracy-Week 4 |  | 97.0833 | 5.52591 | 36 |
|  | Placebo | 97.1429 | 5.51573 | 28 |
|  | Total | 97.1094 | 5.47757 | 64 |

There was also a trend towards statistical significance (p=0.09) for the number of outliers during the spatial working memory task. Outliers indicate lapses in concentration over the duration of the task. As can be seen in the table below, participants in the Procera treatment group showed less mean number of such lapses during the task and were therefore better able to focus and concentrate/process during the spatial working memory task which is a complex cognitive task.

|  | Condition | Mean | Std. Deviation | N |
|---|---|---|---|---|
| Spatial Working Memory-Outliers-baseline | Procera AVH | 1.0256 | 1.03840 | 39 |
|  | Placebo | .7813 | .83219 | 32 |
|  | Total | .9155 | .95139 | 71 |
| Spatial Working Memory-Outliers-week 4 | Procera AVH | .7179 | 1.02466 | 39 |
|  | Placebo | .9063 | 1.20106 | 32 |
|  | Total | .8028 | 1.10350 | 71 |

Numerical Working Memory: Participants on the Procera treatment showed statistically significant improvement (p=0.03) in Numerical Working Memory Accuracy compared to placebo participants. A statistically significant improvement in holding numbers in working memory (immediate memory) was shown from Baseline to Week four due to the Procera treatment.

| Condition | | Mean | Std. Deviation | N |
|---|---|---|---|---|
| Numeric Working Memory Original Stimuli-Accuracy-baseline | Procera AVH | 93.7653 | 5.14656 | 36 |
| | Placebo | 95.7787 | 5.26386 | 30 |
| | Total | 94.6805 | 5.25784 | 66 |
| Numeric Working Memory Original Stimuli-Accuracy-week 4 | Procera AVH | 95.4333 | 3.39970 | 36 |
| | Placebo | 95.0380 | 3.94556 | 30 |
| | Total | 95.2536 | 3.63433 | 66 |

Picture Recognition: There was no significant change in performance in Picture Recognition over the 4 week trial attributable to either Placebo or Procera treatment.

Word Recognition: Word Recognition Accuracy improved for the Procera participant group but decreased for the Placebo participant group across the 4 weeks of the trial. Although this approached statistical significance (p=0.12) this results suggests that Procera improves the accuracy of memory consolidation of words.

| Condition | | Mean | Std. Deviation | N |
|---|---|---|---|---|
| Word Recognition Original Stimuli-Accuracy-baseline | Procera AVH | 73.3336 | 16.25226 | 36 |
| | Placebo | 74.2534 | 14.87757 | 19 |
| | Total | 73.7440 | 15.54023 | 65 |
| Word Recognition Original Stimuli-Accuracy-week 4 | Procera AVH | 75.1853 | 15.50148 | 36 |
| | Placebo | 73.1038 | 14.19566 | 29 |
| | Total | 74.2566 | 14.85472 | 65 |

Word Recognition: The speed of performance during the Word Recognition task was significantly improved (p=0.02) for participants on the Procera treatment compared to the placebo treatment over the 4 weeks of administration. This indicated that Procera significantly improved memory consolidation processes and in particular the speed at which a participant was able to consolidate and access new memories into long term storage.

| Condition | | Mean | Std. Deviation | N |
|---|---|---|---|---|
| Word Recognition Original Stimuli-Speed: Mean-baseline | Procera AVH | 853.1267 | 184.99467 | 36 |
| | Placebo | 774.9913 | 122.44679 | 30 |
| | Total | 817.6106 | 163.26059 | 66 |
| Word Recognition Original Stimuli-Speed: Mean-week 4 | Procera AVH | 757.5228 | 138.40862 | 36 |
| | Placebo | 750.5463 | 147.03377 | 30 |
| | Total | 754.3517 | 141.32551 | 66 |

Inspection Time: A small sub set of participants completed this task. No differences were observed between the Procera and placebo groups but this may be due to the low sample size.

Raven Progressive Matrices: Participants in the Procera group scored statistically higher (p=0.02) on the Raven Progressive Matrices at the end of the 4 week trial than did placebo participants, The Placebo and Procera group were not statistically different at baseline suggesting that 4 week administration of Procera improves general reasoning, visual problem solving and object working memory. This result supports the improvement in spatial and numerical working memory shown in the trial.

| Condition | | N | Mean | Std. Deviation | Std. Error Mean |
|---|---|---|---|---|---|
| Raven's-advance progressive matrix-baseline | Procera AV | 30 | 11.1000 | 2.57776 | .47063 |
| | Placebo | 22 | 10.5000 | 2.54015 | .54156 |
| Raven's-advance progressive matrix-w 4 | Procera AV | 30 | 11.2667 | 3.24763 | .59293 |
| | Placebo | 24 | 9.4167 | 3.38689 | .69135 |
| Raven's-advance progressive matrix-T | Procera AV | 33 | 21.3030 | 5.74176 | .99951 |
| | Placebo | 26 | 18.4615 | 6.09413 | 1.19516 |

It should be noted that the Raven Progressive Matrices Set that was administered to both groups at 4 weeks was significantly harder than the set administered to the two groups at baseline.

Mood Measures Depression (p=0.06): The Procera group showed a decrease in depression scores relative to the placebo group. This suggests that Procera may improve depressive mood.

| Treatment | | Mean | Std. Deviation | N |
|---|---|---|---|---|
| depression dejection baseline (POMS) | Procera AVH | 8.0000 | 9.42388 | 43 |
| | Placebo | 5.1935 | 8.54174 | 31 |
| | Total | 6.8243 | 9.11172 | 74 |
| depression dejection Week 4 (POMS) | Procera AVH | 4.3256 | 5.12566 | 43 |
| | Placebo | 4.3548 | 6.57038 | 31 |
| | Total | 4.3378 | 5.73209 | 74 |

Vigor (p=0.10): The Procera group showed an improvement in Vigor over the 4 weeks of the trial relative to the placebo group.

| Treatment | | Mean | Std. Deviation | N |
|---|---|---|---|---|
| vigor baseline (PDMS) | Procera AVH | 18.140 | 5.4711 | 43 |
| | Placebo | 17.581 | 6.5359 | 31 |
| | Total | 17.905 | 5.9037 | 74 |
| vigor Week 4 (PDMS) | Procera AVH | 19.5116 | 6.38589 | 43 |
| | Placebo | 17.2903 | 6.72901 | 31 |
| | Total | 18.5811 | 6.57935 | 74 |

Anger Hostility (P<0.03): The Procera group showed a statistically significant decrease in anger-hostility over the 4 week trial relative to the placebo group. This indicates that 4 week treatment with Procera significantly improves feelings of anger and hostility. This result is supportive of the decrease in depression scores.

| Treatment | | Mean | Std. Deviation | N |
|---|---|---|---|---|
| anger hostility baseline (POMS) | Procera AVH | 7.8372 | 7.56222 | 43 |
| | Placebo | 4.4839 | 5.80730 | 31 |
| | Total | 6.4324 | 7.03821 | 74 |
| anger hostility Week 4 (POMS) | Procera AVH | 4.1628 | 4.30907 | 43 |
| | Placebo | 3.8065 | 6.12329 | 31 |
| | Total | 4.0135 | 5.11108 | 74 |

Confusion (p=0.06): Participants in the Procera group also showed a decrease in confusion over the 4 week trial which was greater than the placebo participants. Again this result is consistent with the decrease in depression and anger hostility shown by the Procera participants over the 4 week trial.

|  | Treatment | Mean | Std. Deviation | N |
|---|---|---|---|---|
| confusion baseline (POMS) | Procera AVH | 8.9302 | 4.74791 | 43 |
|  | Placebo | 7.5806 | 3.42320 | 31 |
|  | Total | 8.3649 | 4.27024 | 74 |
| confusion Week 4 (POMS) | Procera AVH | 6.1628 | 3.01528 | 43 |
|  | Placebo | 6.5161 | 3.94859 | 31 |
|  | Total | 6.3108 | 3.41602 | 74 |

Total Mood Disturbance (p=0.02): Participants in the Procera group showed a highly statistically significant reduction in mood disturbance over the 4 week duration of the trial relative to the placebo participants. This result indicates that 4 week Procera treatment is highly beneficial for improving mood.

|  | Treatment | Mean | Std. Deviation | N |
|---|---|---|---|---|
| Total mood disturbance score BL (POMS) | Procera AVH | 65.9302 | 30.50870 | 43 |
|  | Placebo | 52.9032 | 23.86120 | 31 |
|  | Total | 60.4730 | 28.48466 | 74 |
| Total mood disturbance score Week 4 (POMS) | Procera AVH | 47.5581 | 17.16905 | 43 |
|  | Placebo | 46.5161 | 26.53158 | 31 |
|  | Total | 47.1216 | 21.42777 | 74 |

Procera Study Summary

The initial results of this study clearly indicate that contemplated formulations of Huperzine, Vinpocetine, and Acetyl-L-Carnitine improve both cognition and mood in healthy participants aged 25-60 years. Statistically significant improvements in several variables relative to placebo could be attributed to the 4 week administration of Procera, and particularly Numerical Working Memory Accuracy (working memory), Word Recognition Speed (long term memory consolidation), Anger-Hostility (mood), Total Mood Disturbance (mood), and Raven Progressive Matrices (fluid intelligence, general reasoning and spatial and object working memory). Placebo was a sugar pill.

The study also found some evidence approaching statistical significance of the following measures to be improved due to the 4 week Procera treatment: Spatial Working Memory Accuracy (working memory), Depression (mood), Confusion (mood), and Vigor (mood).

Figure 4:
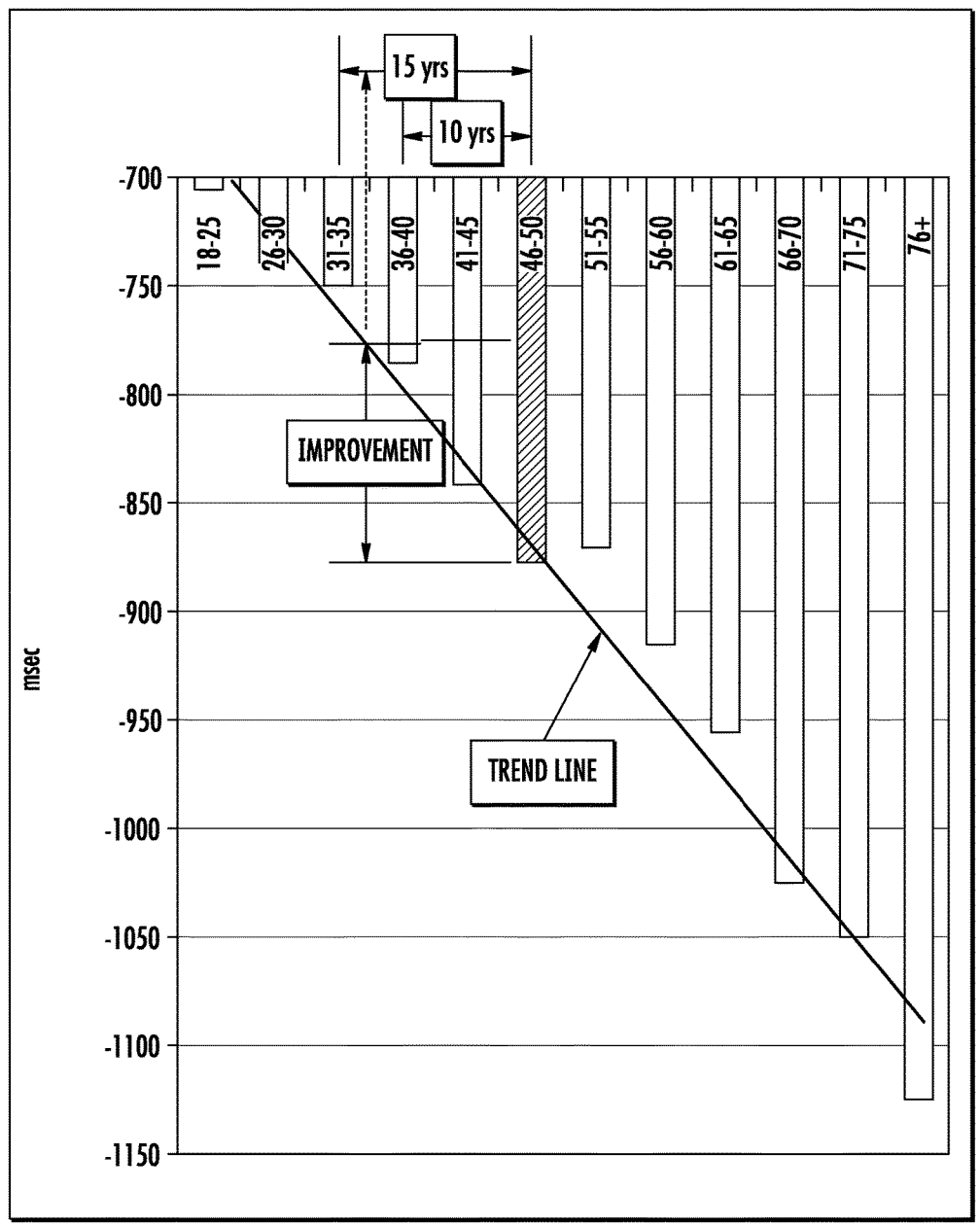
FIG. 4 shows a bar chart of age-related improvements and speed of memory retrieval with the composition in accordance with a non-limiting example.
Figure 5:
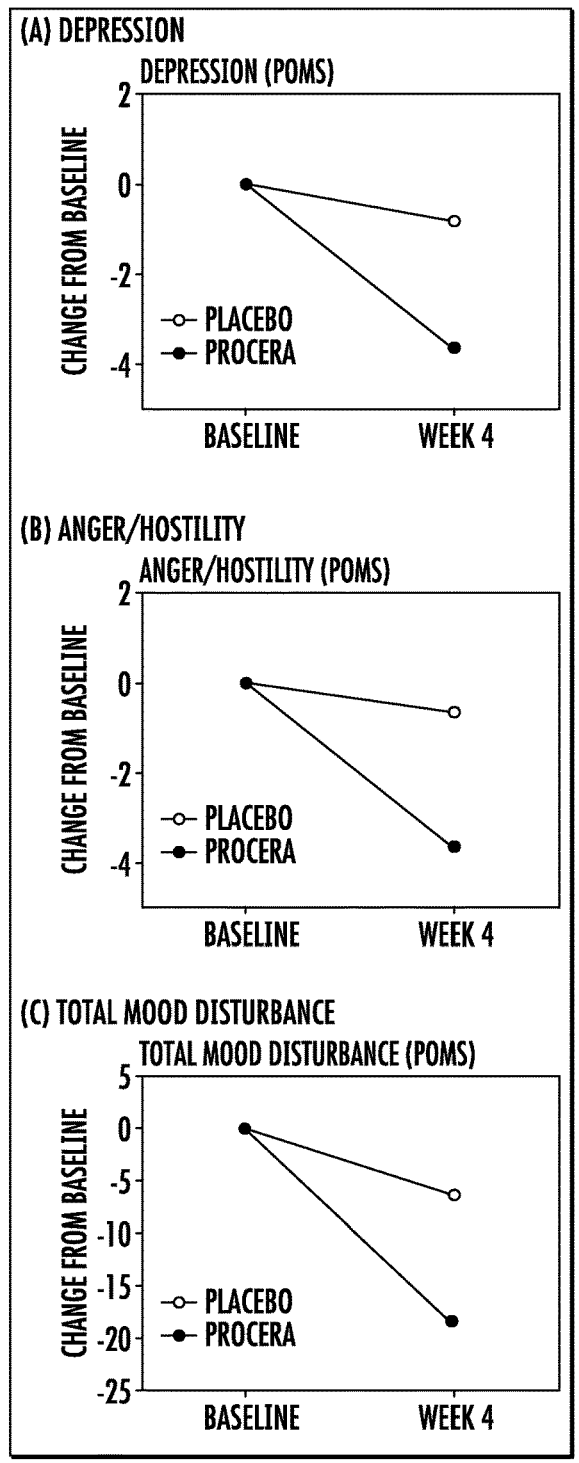
FIG. 5 are graphs showing the changes in mood variables for a placebo and the Procera AVH composition in accordance with a non-limiting example.

FIGS. 1-5 are various figures showing the cognitive tests and outcome variables and results from the more complete clinical trial in the JANA incorporated by reference article. FIG. 1 shows cognitive tests used in testing and FIG. 2 shows the means and standard deviations for significant outcome variables at baseline. FIGS. 3-5 show various test results as explained below.

There now follows further details and the more complete analysis of the original Swinburne University Study identified above and now explained in greater detail below.

Participants: Ninety participants (45 in each of the two groups) were initially enrolled into the 30 day chronic study. Seventy-four (74) participants completed the 30 days and were tested at both baseline and at 30 days (43 in the combination nutraceutical formula group and 31 in the control group). The mean age of the combination nutraceutical formula group was 49.5 years (SD=1.6 22-66 years) and the mean age of the placebo group was 47.1 years (SD=1.9 24-62) years. There was no significant difference in the number of males or females who participated in the study.

Inclusion/Exclusion Criteria: Each participant underwent an individual screening appointment with a registered nurse. Screening incorporated a medical history and cognitive assessment. Participants were eligible if they were aged between 22 and 66 years of age. Exclusion criteria included the following: not currently taking prescription drugs affecting the brain or nervous system (e.g., Modafinil, acetylcholinesterase inhibitors, anticholinergics, stimulants, L-dopa, MAO inhibitors, NMDA receptor antagonists, methylphenidate, amphetamine, pseudo-ephedrine, SSRIs and other antidepressant medication); not currently taking OTC medications affecting the brain (e.g., ephedra based diet pills); those who have not used any supplements within the past 30 days that have an effect on cognitive function, memory, anxiety, depression (e.g. Ginseng, *Gingko*, Vinpocetine, 5HTP, Tryptophan, St. John's Wort, ephedrine (ephedra), alpha GPC, Citicoline, phosphatidylserine, acetyl-1-carnitine, Focus Factor'); not active smokers; not taking the following: anticoagulant drugs (Warfarin, Heparin, Plavix); anti-cholinergics or acetylcholinesterase inhibitors (bethanechol, Ureholine), donepezil (Aricept), rivastigmine (Exelon), galantamine (Reminyl), edrophonium (Enoln, Reversol, Tensilon), neostigmine (Prostigmin); do not have any of the following health conditions: AIDS, HIV, chronic fatigue syndrome, Epstein-Barr, fibromyalgia, lupus, multiple sclerosis, thyroiditis, ulcerative colitis, Crohn's disease, irritable bowel syndrome, dementia including Alzheimer's and Parkinson's disease, Type 1 or 2 diabetes, insomnia or sleep apnea, narcolepsy; no history of head trauma; no neurological deficits; not pregnant or lactating; not anticipating any planned changes in lifestyle (e.g. exercise regimen) for the duration of the study; and no known allergies to nuts.

Study Design: The study was a randomized double blind placebo-controlled design in which participants were allocated either a daily dose of the combination nutraceutical formula or placebo for 30 days. The dose was 1,515 mg per day and each participant was instructed to take 4 pills per day. The combination nutraceutical formula was the Procera AVH.

Measures: Several cognitive and psychological measures were assessed at baseline and at 30 days.

Cognitive Testing: The CDR® program is an automated computerized cognitive assessment system, which has been used in more than 250 published clinical drug studies. The CDR system comprises a battery of cognitive tests that are sensitive to the effects of psychopharmacological substances. The CDR system profiles and assesses a range of cognitive functions, including attention, information processing, sub-loops of working memory, reasoning, secondary memory and skilled coordination. All tasks in the battery are computer controlled, with information being presented on high-resolution monitors, and the responses recorded via a response module containing two buttons, one marked 'YES,' the other marked 'NO.' The versions of the tests specified for elderly participants were employed. The selected battery took the participants around 30 minutes to complete and parallel forms of the tasks were presented at subsequent testing sessions. The cognitive tests used from the battery are presented in the table of FIG. 1. The Profile of Mood States (POMS) is a self-report designed to measure six dimensions of mood: tension/anxiety; depression/dejection; anger/hostility; vigor/activity; fatigue/inertia; and confusion/bewilderment.

Procedure: At baseline each participant completed a general health assessment, which included blood pressure, height and weight, and were then randomly allocated into one of the two treatment groups. They then completed a CDR practice session, which is required in order to become familiar with the tests. After completing the practice session, they were administered the cognitive and psychological tests. Thirty days after their first visit, they completed cognitive and psychological testing again.

Results: A series of repeated measures (ANOVAs) were calculated to examine the changes between baseline and 30 days administration of the combination nutraceutical formula and placebo on the cognitive and psychological measures. As this was the first clinical trial combining the three components in the combination nutraceutical formula, we report the statistically significant analyses ($p<0.05$) as well as the analyses approaching statistical significance ($p$ $0.05<0.10$), which will help the design of future studies assessing this compound.

(1) COGNITION: Non-significant changes in simple reaction time, digit vigilance and choice reaction time, spatial working memory and picture recognition, (long term memory consolidation of objects), were observed over the 30 days administration of the trial. However, 30 days administration of the combination nutraceutical formula (compared to placebo) improved a range of cognitive processes. Means and SDs for these variables are reported in the table of FIG. 2.

Numeric Working Memory: Participants on the combination nutraceutical formula treatment showed statistically significant improvement ($p>0.03$) in numeric working memory accuracy compared to placebo participants. A statistically significant improvement in holding numbers in working memory (immediate memory) was shown from baseline to day 30 due to the combination nutraceutical formula treatment as shown in FIG. 3.

Spatial Working Memory: There was also a trend towards statistical significance ($p<0.09$) for the number of outliers during the spatial working memory task. Outliers indicate lapses in concentration over the duration of the task. Participants in the combination nutraceutical formula treatment group showed less mean number of such lapses during the task and were therefore better able to focus and concentrate/process during the spatial working memory task, which is a complex cognitive task.

Word Recognition: The speed of performance during the word recognition task was significantly improved ($p<0.02$) for participants on the combination nutraceutical formula treatment compared to the placebo treatment over the 30 days of administration (FIG. 1). This indicated that the combination nutraceutical formula significantly improved memory consolidation processes and in particular, the speed at which a participant was able to consolidate and access new memories into long term storage (FIG. 3). As extensive age related normative data are available for the speed of recognition task from the CDR battery, it was possible to calculate the approximate improvement in relative age related functioning due to the combination nutraceutical formula treatment. An improvement in RT of approximately 100 msec was seen in the Procera group compared to approximately 20 msec in the placebo group. Given that the mean age of the group was 48 years, a net improvement of approximately 80 msec on this task (measuring speed of long term memory retrieval) equates to approximately the functioning of age bands some 10-15 years younger (FIG. 4).

(2) MOOD. Depression: The combination nutraceutical formula group showed a decrease in depression scores relative to the placebo group ($p<0.06$). This suggests that the combination nutraceutical formula may improve depressive mood conditions.

Anger/Hostility: The combination nutraceutical formula group showed a statistically significant ($p<0.03$) decrease in anger/hostility over the 30 days trial relative to the placebo group. This indicates that 30 days of treatment with the combination nutraceutical formula significantly improves feelings of anger and hostility. This result is supportive of the decrease in depression scores.

Confusion: Participants in the combination nutraceutical formula group also showed a decrease in confusion over the 30 days trial ($p<0.06$), which was greater than in the placebo participants. Again, this result is consistent with the decrease in depression and anger/hostility shown by the combination nutraceutical formula participants over the 30 days trial. A decrease in confusion may be best understood in terms of improving mental clarity.

Vigor: A non-significant change in vigor scores were observed across the 30 days of the trial ($P<0.10$). An improvement in vigor may be best understood in terms of increased mental energy.

Total Mood Disturbance: The main factor score relating to negative moods on the POMS is total mood disturbance. This factor may be regarded as a highly reliable indicator of changes in negative emotions or moods over the 30 days of supplementation. There was a highly significant change in the total mood disturbance over the 30 days in favor of the combination nutraceutical formula group compared to the placebo group ($p<0.02$). This improvement in mood due to the combination nutraceutical formula is consistent with the observed changes in depression, anger/hostility, confusion and vigor. The result also suggests that changes in mood due to the combination nutraceutical formula are highly noticeable in the participants. FIG. 4 displays the changes from baseline over the 30 days treatment for the combination nutraceutical formula and placebo groups.

Safety: there were no statistical differences in side effects between the two conditions after 30 days of administration.

Alternative Formulation Summary

Remarkably, cognition and mood in healthy participants was not improved in statistically significant manner or even in a manner approaching statistical significance. Study design for this formulation was substantially as outlined below under the section "Additional Comparative Examples."

It should be noted that the overall compositions and respective amounts of ingredients of the comparative composition and contemplated compositions were relatively similar, but did produce significantly different results. Indeed, while the comparative composition failed to provide any measurable advantage (no significant effects on mood, mental clarity or memory, either working memory or longer term memory consolidation or processing speed), or IQ (fluid intelligence), contemplated compositions were statistically significant in a controlled clinical trial. This is especially unexpected as DMAE and selected B vitamins of the comparative composition were thought to be important contributors to and co-factors for a cholinergic enhancement effects of the acetyl-1-carnitine and Huperzine A.

Without wishing to be bound by any theory or hypothesis, it is contemplated that various factors may have contributed to the above difference. For example, the comparative composition may over stimulate neuro-cognitive brain cell receptors, in effect undermining cognitive function and behavior (e.g., mood). This is often seen with pharmaceutical agents that over stimulate brain cells, thus down regulating receptor sensitivity and/or density in the corresponding neurotransmitter system, or neuro-cognitive brain area. Downregulation in any neurotransmitter system can cause swift and ultimately debilitating declines in cognitive and/or psychological (mental health) functions, e.g., memory and mood, respectively.

Moreover, the additional ingredients, even though promising on paper, somehow reduce neural-cognitive function and/or or attenuate or cancel the Procera effect of the comparative composition. In this context, it should be noted that there are many putative cognitive enhancers on the market that claim clinical proof based on presence of multiple active ingredients. Such enhancers will likely suffer from the same drawback as the comparative composition, or have the active ingredients in minute quantities present that will not have any perceivable effect.

Additional Comparative Examples

Chronometric (brain speed) testing can identify what information processing stage is impacted by the therapeutic agent. This may include: motor reflexes (physical reaction time); perceptual acuity; executive function (decision-making speed) and attention; alertness; mental agility (fluid intelligence), and memory (immediate & delayed).

The following CogCAM™ tests were used: CogCAM 4 Working Memory Speed (decision-making; task-shifting); CogCAM10A Memory Scanning (semantic; letters); CogCAM 108 Memory Scanning (visual-spatial; symbols); CogCAM 1 physical reflexes (simple reaction time; attention). These tests provide primary measures of attention, memory and executive cognitive function.

Inclusion Criteria: Male, and non-pregnant (self reported) female subjects, 18 years of age or older, no planned change in lifestyle including exercise regimen during study.

Exclusion Criteria: 1. Taking prescription drugs affecting the brain or nervous system within two weeks of study entry (e.g. epilepsy, Alzheimer's disease, Parkinson's disease, anxiety, depression, psychosis, ADD or other psychiatric condition); 2. Taking OTC medications affecting the brain within two weeks of study entry (e.g. diet pills); 3. Taking supplements known to have an effect on cognitive function, memory, anxiety, depression within two weeks of study entry (e.g. Arctic root or *Rhodiloa*, Ginseng, *Gingko*, Vinpocetine, 5HTP, St. John's wort, ephedrine (ephedra), phosphatidyl choline, phosphatidyl serine, alpha GPC, acetyl-1-carnitine); 4. Smokers.

Formulation C

| | |
|---|---|
| Vinpocetine | 20 mg |
| Pantothenic Acid (Vit. B-5) | 250 mg |
| Dimethylaminoethanol | 300 mg |
| Thiamin (Vit. B-1) | 250 mg |
| Niacin (Vit. B-3) | 20 mg |

Formulation E

| | |
|---|---|
| Huperzine A | 150 mcg |
| Vinpocetine | 20 mg |
| Pantothenic Acid (Vit. B-5) | 250 mg |
| Dimethylaminoethanol | 300 mg |
| Thiamin (Vit. B-1) | 250 mg |
| Niacin (Vit. B-3) | 20 mg |
| Acetyl L Carnitine | 1000 mg |

Methods and Results

To assess the influence of multiple formulations of Formulation C and E on cognitive function, a battery of web-based tests (the Cognometer) was administered over a 6-week treatment period. An analysis of the data compared baseline performance to subsequent weekly exams with placebo or 1 of 5 formulations taken daily to determine if there was a change in cognitive function after initiation of treatment with the dietary supplement compounds in cognitively intact individuals 18 to 74 years of age.

Cognitive performance measures were obtained from web-based assessments using the Cognometer test battery subtests; 4-Executive function and 10-Immediate Memory. There were 2 treatment groups and one control group in this study. The group conditions remained blinded in these analyses, the analyses were completed without knowledge of which groups received the test compounds or placebo. Only individuals who completed tests in each of week (e.g., baseline and all dosing weeks) were included in the analysis. Outliers who scored more than two standard deviations from the mean on a test, and were not internally consistent with other test scores were also eliminated. The elimination of outliers was done to avoid including results that may be due to distractions or web/computer glitches that could invalidate the to particular test session. Analysis of the data uses an analysis of variance (ANOVA) for the differences between the baseline and last week of treatment.

Results and Statistical Analysis

The current trial used the internet to recruit, qualify, register and test over 1000 subjects with 430 completing the 6 week study. Testing was conducted at week 0, Baseline, and every subsequent testing and reporting week for 6 weeks during which subjects were administered the test compounds. On each test day subjects also completed adverse event forms, questionnaires concerning any changes in lifestyle factors, and cognitive testing.

Following is a description of the Cognometer Tests 4 and 10 used in the testing of the compounds and the interpretative data and possible claims that improvement in these tests represent and support.

Test 4 is a "complex choice reaction time task" that tests so called executive cognitive function, or decision making performance speed measured in milliseconds (ms). It has an added unique feature of a random rule reversing cue which tests both one's ability to rapidly inhibit one mode of response and switch to another response mode, considered a higher order cognitive function. Facility in "inhibition and task shifting" can be equated to mental flexibility. Improvement in reaction time on this test supports the claims of: improved mental quickness and flexibility; improved decision making; improved decision making speed; improved cognitive processing; improved decision making speed in a demanding cognitive task.

Test 4 RT data can also be analyzed to assess the group's level of focus, or attention. This measure is derived from computing the standard deviation of the individual's intra trial reaction times (RTSD). This basically represents the consistency of their responses (processing efficiency) and is considered to reflect the level of sustained attention. Improved performance on this score, that is RTSD, supports claims of: improved attention or focus; improved attention or focus on a demanding cognitive task.

Test 10 is divided into two tests, recognition recall of letters and spatial patterns. Only the visuo-spatial memory part of this test showed significance. This test is patterned after the Sternberg Memory Scan paradigm wherein immediate and short term memory processing (scanning & recall) speed equates to memory encoding. Sternberg-like tests, like Cognometer Test 10, have been used for over 30 years in clinical trials and pharmaceutical research to determine drug effects on memory processes. Improved reaction times on this test support claims of: improved memory; improved memory processing speed; improved encoding of information; improved recall speed.

The most notable, however, statistically insignificant effects were found in the 35 plus age group, probably suggesting that the compounds may be effective in those who are beginning to exhibit normal age related slowing associated with increased years of life, typically after 30 years of age. Reaction time standard deviation (RTSD) for this test of executive function did not show a significant difference between groups. The reaction time median scores (RTmed), a measure of executive function (decision making and mental flexibility) did also not indicate significant between group differences.

Selected results are as follows, with group A taking placebo, group C taking Formulation C, and group E taking C Formulation E.

RT Median—Test 4

| Group | Mean | SEM |
|---|---|---|
| A | 91.509 | 2.498 |
| C | 88.315 | 2.343 |
| E | 94.505 | 2.352 |

RT Standard Deviation—Test 4

| Group | Mean | SEM |
|---|---|---|
| A | 85.045 | 5.695 |
| C | 89.4 | 4.588 |
| E | 88.8 | 5.506 |

RT Median (Shapes)—Test 10

| Group | Mean | SEM |
|---|---|---|
| A | 91.523 | 2.016 |
| C | 95.698 | 2.797 |
| E | 93.103 | 2.093 |

Thus, no significant improvement in cognitive functions was observed with those formulations tested. Such finding is once more remarkable as the formulations appear to have similar compositions, but significantly different effects in toto.

Ceretrophin Clinical Study and Results

A clinical study was conducted in healthy human participants by the Brain Sciences Institute, Swinburne University in Australia on Ceretrophin (see Formulation II above). Approximately 100 participants were initially enrolled into the clinical study. Human cognition is complex but can be measured using standardized tests of information processing, reaction time, attention, concentration, working memory, long term memory and decision making. These standardized measures relate to how human perform simple and complex tasks in real life. By assessing a range of cognitive measures before and after one month administration of either Ceretrophin or placebo, remarkable results were achieved as provided in more detail below.

Study Methodology: The study was a randomized, double-blind, placebo controlled study examining the effects of a special nutritional formulation Ceretrophin vs placebo on cognitive function and mood. This means that the participants were randomly allocated to either a placebo or Ceretrophin group in which they were administered either placebo or Ceretrophin tablets for one month. The study was double blind because both the experimenters and the human participants did not know which tablets they were taking.

Exclusion Criteria: 1. Not currently taking prescription drugs affecting the brain or nervous system (e.g., Modafinil, acetylcholinesterase inhibitors, anti-cholinergics, stimulants, Ldopa, MAO inhibitors, NMDA receptor antagonists, methylphenidate, amphetamine, pseudo-ephedrine, SSRIs and other anti-depressant medication), 2. Not currently taking OTC medications affecting the brain (e.g., ephedra based diet pills), 3. Who have not used any supplements within the past 30 days that have an effect on cognitive function, memory, anxiety, depression (e.g. Ginseng, Gingko, Vinpocetine, 5HTP, Tryptophan, St. John's Wort, ephedrine (ephedra), alpha GPC, Citicoline, phosphatidylserine, acetyl-L-carnitine, Focus Factor), 4. Not active Smokers. 5. Not taking the following: anti-coagulant drugs (Warfarin, Heparin, Plavix); anticholinergics or acetylcholinesterase inhibitors (bethanechol (Ureholine), donepezil (Aricept), rivastigmine (Exelon), galantamine (Reminyl), edrophonium (Enoln, Reversol, Tensilon), neostigmine (Prostigmin) 6. Do not have any of the following health conditions: AIDS, HIV; to Chronic Fatigue Syndrome, Epstein Barr, Fibromylagia, Lupis, Multiple Sclerosis, Thyroiditis, Ulcerative Colitis, Crohn's Disease, Irritable Bowel Syndrome, dementia including Alzheimer's and Parkinsons' disease, Type 1 or 2 Diabetes, Insomnia or Sleep Apnea, Narcolepsy 7. No history of head trauma 8. No neurological deficits 9. Not pregnant or lactating 10. Not anticipating any planned changes in lifestyle (e.g. exercise regimen) for the duration of the study 11. No known allergies to nuts 12. Must not be younger than 18 years of age or older than 65 years of age.

In addition participants were requested not to have alcohol or caffeine-containing food or beverages on the testing days (e.g., coffee, tea, chocolate and energy drinks containing caffeine or guarana). Further to control for food intake participants they were also required to eat a light breakfast (e.g., 2 pieces of toast or cereal with juice) on the testing days.

Test Parameters: The following neuropsychological tests were employed in the currents study: The Cognitive Drug Research measure (CDR) is a well-validated test, which was used to assess attention, working memory and episodic secondary (longer term memory, or consolidation). Inspection time (IT) is a measure speed of early information processing. The Profile of Mood States (POMS) is a self-report designed to measure six dimensions of mood: tension-anxiety; depression-dejection; anger-hostility; vigor-activity; fatigue-inertia; and confusion-bewilderment (POMS: McNair, Lorr, & Droppelman, 1992).

IQ was assessed using the Raven's Progressive Matrices. This was done by administering the even items at baseline and the odd items at Week 4. The UWIST Mood Adjective Checklist (UMACL; Matthews, Jones & Chamberlain, 1990) will be used to Measure mood states and energy levels. The Spielberger State-Trait Anxiety Inventory (STAI: Spielberger, 1983) is a 20-item questionnaire, to measure anxiety at the time of testing. Perceived Stress Scale (PSS; Cohen, 1983) was used to measure stress symptoms and effective coping Participants visited Swinburne University on 3 separate occasions Visit 1: Health assessment, practice, baseline and acute testing Visit 2: 1 week (7 days) following baseline testing and Visit 3: 4 weeks (28 days) following baseline testing. During the first visit, participants completed a general health assessment and were then allocated into one of three treatment groups for baseline and acute testing.

Results

Cognitive Measures: Raven Progressive Matrices (general intelligence IQ): Participants in the Ceretrophin group statistically improved their performance on the Raven Progressive Matrices relative to the placebo group ($p<0.001$). This was a very strong effect and equates to an IQ improvement of about 6 IQ points. The Raven Progressive Matrices is a well-validated non-verbal measure of general intelligence. To complete this task a participant must engage in several higher order cognitive processes such as visualization, spatial working memory, mental rotation, reasoning, and non-verbal problem solving. This is a remarkable result particularly given the statistical significance and effect size. This result supports the smaller improvements in accuracy of the less difficult tasks used in the CDR battery. It is of note that the most significant effect of Ceretrophin is seen with the most complex task. Future studies may wish to use highly complex cognitive tasks in order to ascertain the full potential of Ceretrophin on the brain and cognition.

| | Condition | Mean | Std. Deviation | N |
|---|---|---|---|---|
| Raven's advance progressive matrix - baseline | Ceretrophin | 8.2500 | 3.34984 | 36 |
| | Placebo | 9.3929 | 3.77457 | 28 |
| | Total | 8.7500 | 3.55903 | 64 |
| Raven's advance progressive matrix - week 4 | Ceretrophin | 9.7500 | 3.47542 | 36 |
| | Placebo | 8.1786 | 4.49735 | 28 |
| | Total | 9.0625 | 3.99950 | 64 |

Simple Reaction Time: The speed of simple reaction time did not significantly improve due to the Ceretrophin treatment across the 4 weeks of administration. This is the simplest cognitive measure in the cognitive battery. This result is consistent with the results from the other main variables in so far as the Ceretrophin™ did not speed up neural processes but instead improved accuracy and reduced mistakes.

Digit Vigilance and Choice Reaction Time: The Ceretrophin treatment significantly ($p=0.05$) decreased the number of false alarms (mistakes) during the Digit Vigilance task after 4 week administration. Participants in the Ceretrophin group relative to the placebo group improved their attention/concentration. This was a relatively strong effect.

| | Condition | Mean | Std. Deviation | N |
|---|---|---|---|---|
| Digit Vigilance - False Alarms - BASELINE | Ceretrophin | 1.0513 | 1.19095 | 39 |
| | Placebo | .6129 | 1.05443 | 31 |
| | Total | .8571 | 1.14570 | 70 |
| Digit Vigilance - False Alarms - Week 4 | Ceretrophin | .7436 | .78532 | 39 |
| | Placebo | .7742 | 1.02338 | 31 |
| | Total | .7571 | .89176 | 70 |

Performance on the Choice Reaction Time Accuracy also improved due to the Ceretrophin™ and this result approached statistical significance ($p=0.11$). The effects of the Ceretrophin was not to speed up the brain directly or to make participants quicker to respond to the discrimination but gave them better accuracy in discriminating between the stimulus alternatives. This indicates an improvement in the efficiency of decision making and information processing. Note that there was not a slowing of RT which led to an increase in accuracy. The increase in accuracy due to the Ceretrophin was not a consequence of a slowing of response time (increase in RT). Although approaching statistical significance this was not a strong effect.

| | Condition | Mean | Std. Deviation | N |
|---|---|---|---|---|
| Choice Reaction Time - Accuracy - baseline | Ceretrophin | 96.8421 | 2.73640 | 38 |
| | Placebo | 97.4000 | 2.58110 | 30 |
| | Total | 97.0882 | 2.66394 | 68 |
| Choice Reaction Time - Accuracy - Week 4 | Ceretrophin | 97.3158 | 2.42849 | 38 |
| | Placebo | 97.0667 | 3.51287 | 30 |
| | Total | 97.2059 | 2.93491 | 68 |

Spatial Working Memory: There was a trend towards significance for Spatial Working Memory Outliers ($p=0.13$). Although not significant, the results (see mean values below) indicate that there was more of an improvement in the number of mistakes over the treatment duration for the Ceretrophin than for the placebo. Larger sample size may help this result become statistically significant. This result should be treated as a preliminary finding that should be subjected to replication in a larger sample.

| | Condition | Mean | Std. Deviation | N |
|---|---|---|---|---|
| Spatial Working Memory - Outliers - baseline | Ceretrophin | 1.0000 | 1.16190 | 41 |
| | Placebo | .7813 | .83219 | 32 |
| | Total | .9041 | 1.02962 | 73 |
| Spatial Working Memory - Outliers - week 4 | Ceretrophin | .7317 | 1.04939 | 41 |
| | Placebo | .9063 | 1.20106 | 32 |
| | Total | .8082 | 1.11377 | 73 |

Numerical Working Memory: Participants on the Ceretrophin treatment showed an improvement ($p=0.18$) in Numerical Working Memory Accuracy compared to placebo participants. This again approached statistical significance. The result indicates that there is some evidence that there is an improvement in holding numbers in working memory (immediate memory) from Baseline to Week four due to the Ceretrophin treatment. Increasing the sample size (statistical power) may result in this variable showing statistical significance. This is an interesting but preliminary finding.

|  | Condition | Mean | Std. Deviation | N |
| --- | --- | --- | --- | --- |
| Numeric Working Memory Original Stimuli - | Ceretrophin | 92.1645 | 7.24746 | 38 |
|  | Placebo | 95.7787 | 5.26386 | 30 |
| Accuracy - baseline | Total | 93.7590 | 6.65344 | 68 |
| Numeric Working Memory Original Stimuli - | Ceretrophin | 92.6326 | 7.80322 | 38 |
|  | Placebo | 95.0380 | 3.94556 | 30 |
| Accuracy - week 4 | Total | 93.6938 | 6.46620 | 68 |

Picture Recognition: There was no significant change in performance in Picture Recognition over the 4 week trial attributable to either Placebo or Ceretrophin treatment.

Word Recognition: Word Recognition Accuracy improved for the Ceretrophin participant group but decreased for the Placebo participant group across the 4 weeks of the trial. Although this only approached statistical significance ($p=0.12$) the results provides some evidence that Ceretrophin treatment improves the accuracy of memory consolidation of words. Again a systematic picture of results is emerging with many variables showing improvement in accuracy rather than speed, and that this improvement in accuracy is not a consequence of a slowing of RT (or more cautious responding). Overall the changes to the different accuracy variables suggest that the Ceretrophin improves efficiency by reducing the number of errors of neural processing of cognitive measures.

|  | Condition | Mean | Std. Deviation | N |
| --- | --- | --- | --- | --- |
| Word Recognition Original Stimuli - | Ceretrophin | 73.3336 | 16.25226 | 36 |
|  | Placebo | 74.2534 | 14.87757 | 29 |
| Accuracy - baseline | Total | 73.7440 | 15.54023 | 65 |
| Word Recognition Original Stimuli - | Ceretrophin | 75.1853 | 15.50148 | 36 |
|  | Placebo | 73.1038 | 14.19566 | 29 |
| Accuracy - week 4 | Total | 74.2566 | 14.85472 | 65 |

Inspection Time: A smaller sub-set of participants completed this task. No differences were observed between the Ceretrophin and placebo groups but this may be due to the low sample size.

(2) Mood Measures: Perceived Stress ($p<0.05$): Four week treatment of Ceretrophin showed a small reduction in the levels of stress perceived by participants relative to the placebo group. It is also noteworthy that participant recruitment did not involve highly stressed or anxious individuals but just normal population levels of stress and other moods. This effect may be even more pronounced if a more clinical population was tested.

|  | Treatment | Mean | Std. Deviation | N |
| --- | --- | --- | --- | --- |
| Perceived Stress Scale | Ceretrophin | 28.2973 | 3.02641 | 37 |
|  | Placebo | 29.0333 | 3.87283 | 30 |
| baseline | Total | 28.6269 | 3.42378 | 67 |
| Perceived Stress Scale | Ceretrophin | 27.4054 | 3.24431 | 37 |
|  | Placebo | 29.6333 | 3.83705 | 30 |
| Week 4 | Total | 28.4030 | 3.66829 | 67 |

Tense Arousal ($p=0.12$): Consistent with the reduction in the level of stress, we observed a reduction in the level of tense arousal. This was not statistically significant and a larger sample would increase the statistical power with this variable.

Safety: There were no statistically significant side-effects after 4 weeks of testing.

Conclusion of Ceretrophin Study

In terms of the cognitive variables, there is evidence that Ceretrophin improves functioning during highly complex cognitive tasks that assess general reasoning and problem solving. There was also some evidence that Ceretrophin improved working memory variables. The results if taken together do also suggest an improvement in the efficiency of information processing and decision making such as in improving accuracy and reducing cognitive errors. The reduction in errors and improvement in accuracy was seen in nearly all tasks. The highly statistically significant improvement in general intelligence from the Raven Progressive Matrices was larger than the other cognitive variables and so was easily observed statistically (see also Intelligence 39 (2011) 100-107, incorporated by reference herein).

In terms of mood, Ceretrophin appears to reduce stress and tension. Given the increase in occupational stress seen throughout the western world this is an important finding. Overall the results suggest that Ceretrophin is a unique compound that exerts beneficial effects to both cognition and mood, particularly in general intelligence and during complex cognitive reasoning tasks/decision making.

Statistically significant improvements in several variables relative to placebo could be attributed to the 4 week administration of Ceretrophin Raven Progressive Matrices (working memory, general intelligence)

Digit Vigilance Errors (attention)

Stress (mood)

The study also found some evidence (approaching statistical significance) of the following measures to be improved due to the 4 week Ceretrophin treatment Spatial Working Memory Errors (working memory)

Numerical Working Memory Accuracy (working memory)

Word Recognition Accuracy Original Stimuli (memory consolidation)

Tension (mood)

Thus, specific embodiments of nutritional supplements for enhancing cognitive function have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

Procera Extreme Focus (XTF) Composition

The Procera composition as described above includes acetyl-L-carnitine (ALC), vinpocetine and huperzine A and is also referred to as Procera AVH. It has been clinically tested successfully as a cognitive and mood enhancer as shown in the examples above. That composition as the Procera AVH enhances different cognitive functions, including short-term memory recall speed, long-term memory, attention (focus and concentration), and mental clarity and mood. The Procera Extreme Focus (XTF) composition as will be described and referred to as Procera XTF includes those three major components of the Procera AVH, plus additional mental performance boosting, anti-fatigue and anti-stress ingredients, including *Rhodiola* rosea and key B-vitamins as a Vitamin B complex, including Vitamins B3, B5 and B6. This composition also includes a blend of natural sources of caffeine, including a green tea and guarana extract. The caffeine works synergistically with several of the components in the composition, especially vinpocetine.

The Procera XTF composition combines the clinically validated cognitive enhancer of the AVH having the acetyl-L-carnitine, vinpocetine and huperzine A with the benefits of *Rhodiola* rosea for improved mental and physical performance under stressful or challenging condition. The B-vitamins and herbal energy boosting extracts support optimal brain function under peak performance demands. It has been found that specific ingredients and their concentration and ranges enhance the function of each of the ingredients and synergistically helps the brain sustain mental performance longer, including improved concentration, motivation, memory recall and mental energy. The composition is effective for those persons that require the additional help of greater brain power and mental and physical energy while studying in the classroom, board room or participating in an athletic event.

The concentrations and ranges of the AVH ingredients and *Rhodiola* are generally based upon the clinical results explained above. The Procera XTF is an enhanced and clinically proven composition that includes other ingredients that act synergistically with the AVH components and the *Rhodiola* rosea. Niacin as B3 and pantothenic acid as B5 are disclosed as part of the composition for Procera XTF, but were not used in the Cerotrophin composition. Procera XTF includes the additional B-vitamin such as Vitamin B6 that has added neurotransmitter support. Added caffeine is supplied from a guarana seed extract and green tea leaf extract and other natural caffeine sources such as from coffee aribica seeds. The caffeine synergistically enhances the vinpocetine. The *rhodiola* operates as an adaptogen that helps protect the brain from stress such as from cortisol, and has been shown to have potent anti-depressant and anxiolytic effects most likely due to its effects on the monoaminergic system acting as an inhibitor of MAO (monoamine oxidase) A and B. The B-vitamins are mainly in support of the cholinergic and serotonergic systems.

The concentrations and ranges of ingredients are similar to the compositions as described above, but with certain variations that are made optimal for use with this Procera XTF composition. The example nutritional supplement composition for enhancing cognitive function that is formulated as the Procera XTF composition includes the acetyl-L-carnitine, vinpocetine and huperzine A, the B-vitamin complex and the *Rhodiola* with the natural caffeine sources.

In an example, the Procera XTF nutritional supplement composition enhances cognitive function and includes at least huperzine A, vinpocetine, acetyl-L-carnitine, and *rhodiola*. This composition is formulated for oral administration and the huperzine A, vinpocetine, acetyl-L-carnitine, and *rhodiola* are in a ratio a:b:c:d respectively such that a as the huperzine A is between about 0.8 and 1.2, b as vinpocetine is between about 80 and 120, c as *rhodiola* is about 1,600 and 2,400, and d as the acetyl-L-carnitine is between about 8,000 and 12,000. In these examples, the first letters of the alphabet are used for the ratios instead of the last letters as previously done as above.

In one example, the composition includes a Vitamin B complex (e) in a ratio a:b:c:d:e with the huperzine A, vinpocetine, acetyl-L-carnitine, and *rhodiola* such that (e) as the Vitamin B complex is between about 700 and 1,200. The Vitamin B complex is formed as Vitamins B3, B5 and B6 in an example. In another example a green tea and guarana extract (f) is in a ratio a:b:c:d:f with the huperzine A, vinpocetine, acetyl-L-carnitine, and *rhodiola* such that (f) as the green tea and guarana extract is between about 1,600 and 2,400.

In an example, the *rhodiola* is formed of about 2 to 4% rosavins and 0.5 to 1.5% salidrosides. In another example, the huperzine A, acetyl-L-carnitine, vinpocetine, and *rhodiola* together account for at least 80 wt % of a dosage unit of the composition. The huperzine A, vinpocetine, acetyl-L-carnitine, and *rhodiola* are in a ratio to each other in another example such that the huperzine A is between about 0.9 and 1.1, the vinpocetine is between about 90 and 110, the *rhodiola* is between about 1,800 and 2,200, and the acetyl-L-carnitine is between about 9,000 and 10,000.

In an example, the acetyl-L-carnitine is present in an amount from about 1,250 mg to 1,500 mg, the vinpocetine is present in an amount from about 10 mg to 30 mg, the *rhodiola* is present in an amount from about 250 mg to 350 mg, the huperzine A is present in an amount from about 50 mcg to 200 mcg, the green tea and guarana extract is present in an amount from about 250 mg to 350 mg, and the Vitamin B complex is present in an amount from about 125 mg to 175 mg.

In another example, the composition is formulated with an enteric coating and an inactive ingredient may be selected from the group consisting of a carrier, a binder, an excipient, a dye and combinations thereof. A method of assisting enhancement of cognitive function in a person is also included by administering the nutritional supplement composition.

The Procera XTF nutritional supplement composition enhances cognitive function and includes huperzine A, vinpocetine, acetyl-L-carnitine, *rhodiola*, a Vitamin B complex comprising Vitamins B3, B5 and B6, and a green tea and guarana extract. The composition is formulated for oral administration and the huperzine A, vinpocetine, *rhodiola*, acetyl-L-carnitine, each of Vitamins B3, B5 and B6, and the green tea and guarana extract are in a ratio a:b:c:d:e:f respectively such that a as huperzine A is between about 0.8 and 1.2. B as the vinpocetine is between about 80 and 120. C as the *rhodiola* is between about 1,600 and 2,400. D as the acetyl-L-carnitine is between about 8,000 and 12,000. E as each the Vitamins B3, B5 and B6 is between about 250 to 400. F as the green tea and guarana extract is between about 1,600 and 2,400. The Vitamin B3 is formed as Niacin and Niacinamide in one example and Vitamin B5 is formed from pantothenic acid and D-calcium pantothenate.

The Procera XTF nutritional supplement composition in an example enhances cognitive function and includes huperzine A; vinpocetine; acetyl-L-carnitine; *rhodiola*; a Vitamin B complex comprising Vitamins B3, B5 and B6; and a green tea and guarana extract. The composition is formulated for oral administration and the huperzine A is present in an amount from about 50 mcg to 200 mcg, and the vinpocetine is present in an amount from about 10 mg to 30 mg. The *rhodiola* is present in an amount from about 250 mg to 350 mg, and the acetyl-L-carnitine is present in an amount from about 1,250 mg to 1,500 mg. Each of Vitamins B3, B5 and B6 are present in an amount from about 40 mg to 60 mg and the green tea and guarana extract are present in an amount from about 250 mg to 350 mg. The huperzine A, acetyl-L-carnitine, vinpocetine and *rhodiola* together account for at least 80 wt % of a dosage unit of the composition.

The example nutritional supplement composition includes 50 mg of Vitamin B3, which is formulated as 25 mg of niacin and 25 mg of niacinamide corresponding to 250% of a daily value. The composition in the example includes 50 mg of Vitamin B6 as pyridoxine HCL corresponding to a 2,500% daily value. The composition also includes 50 mg of pantothenic acid as D-calcium pantothenate corresponding to 500% of daily value. The acetyl-L-carnitine is about 1,500 mg per serving. The vinpocetine is about 15 mg per serving and huperzine A is about 0.15 mg. The *Rhodiola* rosea is about 300 mg per serving and includes 3% rosavins and 1% salidrosides.

Caffeine is provided by the Guarana seed extract that is 22% caffeine in one example. The green tea leaf extract is 90% caffeine in an example. In another example, the natural caffeine from coffee aribica seeds is about 90% caffeine. The total composition mixture of the *Rhodiola* rosea and the Guarana seed and Green tea leaf extract and other ingredients is about 600 mg. The Guarana seed extract, green tea leaf extract and coffee blend is about 300 mg, which is equal to about 80 mg of caffeine.

There now follows a description of the various ingredients and their functional workings and synergistic relationship. In use, four capsules may be taken 30-60 minutes prior to when needed such as when studying for or taking a large exam or to learn something new, such as a computer program or application, to be quick and focused at an athletic event or video game, or to be sharp and clear headed. Generally, the composition works by increasing the circulation of blood to the brain and delivering the oxygen, glucose and other nutrients to increase the brain's energy or cerebral metabolism to improve brain function and cognitive performance. It also improves key neurotransmitters such as acetylcholine and dopamine to increase sustained focus that is often depleted by stress, sleep loss, poor diet and other physical problems and conditions, including alcohol and aging.

The Procera AVH includes the acetyl-L-carnitine (ALC) that is natural to the body and is found in fish, which is one reason fish is called brain food. The human body manufactures some acetyl-L-carnitine, but it declines sharply with age. The signs and symptoms of low acetyl-L-carnitine can be mood swings, memory loss, poor ability to sustain concentration, mental confusion and fatigue. It is an acetylated form of L-carnitine and is broken down in the blood by plasma esterases to carnitine to transport fatty acids into the mitochondria for breakdown and energy production. The acetyl-L-carnitine and food make the brain more efficient in its energy use.

Vinpocetine is derived from a natural extract found in the periwinkle flower called Vincaminor. It is a neuroprotective antioxidant that helps protect the brain against free radicals caused by neurotoxins, stress, alcohol, junk food and aging. It is a semi-synthetic derivative of the alkaloid vincamine as an extract from the periwinkle plant. It may operate as a vasodilator and a possible anti-inflammatory agent that inhibits the up-regulation of NF-κB. It may selectively inhibit voltage-insensitive $NA^+$ channels to result in a dose-dependent decrease in evoked extracellular $CA^+$ ions and striatal nerve endings. This may reduce the neuroinflammatory processes that cause neuronal death or slow down in chemical transfer in the brain and result in greater brain efficiency.

Huperzine A strengthens memory and addresses the brain's need for the neurotransmitter acetylcholine (ACH) that aids in memory and concentration. It may offer some brain protection against neurotoxic organophsophates. It is sesquiterpene alkaloid and is an acetylcholinesterase inhibitor and NMDA receptor antagonist.

The *Rhodiola* rosea is 3% rosavins and 1% salidrosides. It is a flowering plant that grows in the cold regions of the world and includes 140 chemical compounds with its roots containing phenols, rosavin, rosin, rosarin, organic acids, terpenoids, phenolcarbonic acids and their derivatives, as well as flavonoids, anthraquinones, and alkaloids. Because rosavins is used in the composition at 30%, the *Rhodiola* will probably be of Russian origin and may include rosavin, rosarin, and rosin. Other active ingredients that may be included within the *Rhodiola* rosera include rhodioloside and tyrosol with other components showing some synergy when used with rhodioloside, rosavin, rosarin and rosin. Salidroside is also included and is a polyphenol.

The *rhodiola* may inhibit MAO-A and MAO-B through a monoamine oxidase inhibition mechanism. It is believed that the *rhodiola* promotes the release of norepinephrine to resist senility. The Rosavin is a cinnamyl alcohol glycoside and with salidroside is responsible for antidepressant and anxiolytic actions of the plant. The salidroside is a glucoside of the tyrosl found in the *rhodiola* plant and may be more active than rosavin. *Rhodiola* is a potent adaptogen and helps to keep the brain and body's neurotransmitters and hormones in balance under extreme mental and physical stress conditions. *Rhodiola* is also shown to have potent anti-depressant and anxiolytic (anti-anxiety) effects due to its modulation of serotonin, norepinephrine and possibly dopamine.

A B-vitamin complex includes Vitamins B3, B5 and B6. These B-vitamins help sustain sufficient neurotransmitter levels. Some B-vitamins such as Vitamin B5 as pantothenic acid can be depleted by stress and exhausting mental challenges and raise the need for extra supplementation. The Vitamin B3 includes both niacin and niacinamide. Both are in equal amounts of about 25 mg in one commercial example of the composition.

Niacin is a derivative of pyridine with a carboxyl group (COOH) at the 3 position and the corresponding niacinamide has the carboxyl group replaced by carboxamide group (CONH) and sometimes other amides and esters. Both niacin and niacinamide are precursors of coenzymes nicotinamide adenine dinucleotide (NAD) and nicotinamide adenine dinucleotide phosphate (NADP). The NAD is important not only in catabolism of fat, carbohydrate, protein and alcohol, but also cell signaling and DNA repair NADP is operative in anabolism reactions and fatty acid and cholesterol synthesis. Its ability to inhibit cyclic adenosine monophosphate (CAMP) production and fat breakdown may also be beneficial in brain function. It is also believed that the niacinamide is an activator of sirtuins to aid in restoring cognition. This could be due to preventing apoptosis in cells exposed to agents that induce oxidative stress, and thus, may prevent apoptosis in neuronal cells.

Vitamin B5 as pantothenic acid is included and in one example is D-calcium pantothenate to aid in synthesizing coenzyme-A (CoA) and synthesize and metabolize proteins, carbohydrates and fats. The dextrorotatory (D) isomer of pantothenic acid possesses the biologic activity while the levorotatory (L) form may antagonize the effects of the other enantiomer. A racemic mixture is usually not preferred. The coenzyme-A synthesis is beneficial and acts as an acetyl root carrier to form acetyl-CoA to transport carbon atoms within a cell and operates to increase energy metabolism for pyruvate to enter the tricarboxylic acid cycle. It is also important for biosynthesizing acetylcholine.

The Vitamin B6 as pyridoxine HCL is used for enzymatic reaction governing the release of glucose from glycogen. In vivo, the Vitamin B6 is operative with forming the pyridoxal phosphate-dependent enzymes for biosynethesizing neurotransmitters such as serotonin, dopamine, epinephrine, norepinephrine, and gamma-aminobutyric acid (GABA).

As noted before, there are natural caffeine sources such as the green tea extract and guarana bean extract and natural coffee. Guarana seeds contain about twice the concentration of caffeine found in coffee beans such as 2-4.5% caffeine in guarana seeds as compared to 1-2% in coffee beans. There are many chemicals found in guarana seeds. Primary natural phenols found in guarana include catechin and epicatechin. Catechin is a natural phenol and antioxidant. The catechin and epicatechin are selective monoamine oxidase inhibitors (MAOI) of the type MAO-B and thus may reduce the symptoms of Parkinson's Disease and Alzheimer's patients. Epicatechin is able to cross the blood-brain barrier more efficiently than other agents such as resveratrol, which is more hydrophilic. The catechin may activate BDNF pathways.

Green tea extracts offer additional benefits by obtaining different types of tea catechins, epigallocagethin (EGC), epicatechin gallate (ECG), and epicatechin. There are also different flavonoids such as kaempferol, quercetin, and myricetin. It is more antioxidant active than Vitamin C such as provided by the EGCG. The green tea extracts have better preservation of catechins than black tea extracts and thus are a better anti-inflammatory. Other types of coffee blends may be used although the caffeine content would be less compared to a guarana extract, but would have other components and ingredients that may not be included in the guarana and green tea extracts. About 300 mg of a guarana and green tea extract (with the optional coffee blend) may be used to equal about 80 mg of caffeine.

The ingredients as described for the Procera XTF have been selected in their percentage, concentrations and ranges to operate in the most efficient and best synergistic manner. These percentages, concentrations and ranges have been developed through extensive experimentation as explained above and in subsequent trials and experiments. The niacin in Vitamin B3 creates vasodilation and imparts some flushing that may enhance nutrient delivery to the brain and other parts of the body. The niacinamide in Vitamin B3 contributes to brain energetics at the NAD level. The NAD exists in an oxidized and reduced form as $NAD^+$ and NADH respectively. The niacin and niacinamide compliment the other ingredients and are selected in a specific range to be effective. The B3 and B6 assist for neurotransmitter support with the primary neurotransmitter as serotonin that operates with the $5-HT_3$ receptor. The Vitamin B5 helps synthesize the acetylcholine and may operate as a major cholinergic enhancer, and thus, the B5 works in synergy for cholinergic enhancement. Some propose that the compromise of the cholinergic system causes some Alzheimer's and associated memory loss. Vitamin B5 and its operation may be beneficial since the parasympathetic nervous system uses acetylcholine to send messages. It is believed by some researchers that neurotransmitter imbalances cause Alzheimer's Disease because of a reduced synthesis of acetylcholine. The increased NADH as a result of the Procera XTF may result in a six-fold increase in neurotransmitter dopamine and may produce more growth hormone secretion and increase the body's ability to repair or replace damaged and wounded cells. In Parkinson's Disease, the brain cells that produce dopamine die, and thus, the increase in NADH using the composition as described for the Procera XTF may improve patients that have Parkinson's Disease. The caffeine from the various sources as described has cognitive enhancing effects on mental energy and synergistically enhances the effect of the vinpocetine and creates vasodilation and enhances the update and use of glucose and oxygen.

Through the numerous clinical trials and experiments conducted as explained above and in subsequent work, the Procera XTF formulation has been found to be effective and the range and concentration of ingredients selected for the most optimal performance in brain enhancement. Other components may be added as experiments continue and feedback ensues.

As noted above, the inventor had found through observation and further work that *Ginkgo biloba* may be substituted for vinpocetine and used in combination with the huperzine A and acetyl-L-carnitine in specific ratios and concentration ranges and advantageous results obtained similar as to when the previous composition was used with vinpocetine in combination with the huperzine A and acetyl-L-carnitine to form the Procera AVH composition. Enhancements in short-term memory such as a factor-derived speed of attention factor are believed achievable with the new composition using *Ginkgo biloba* instead of vinpocetine, even when the amounts of *Ginkgo biloba* are reduced from the normally higher amounts evident in some studies for speed of attention to be effective at daily dosages above 240 mg and closer to 360 mg. For example, the higher doses of 240 and 360 mg of the *Ginkgo biloba* extract were shown to result in improvements on a factor-derived "speed of attention" factor, which was evident at 2.5 hours after ingestion, and was still present at 6.0 hours, i.e., Kennedy et al., "The Dose-Dependent Cognitive Effects of Acute Administration of *Ginkgo Biloba* to Healthy Young Volunteers," Psychopharmacology, 2000; 151:416-423. It is believed and based on observation that the current composition with its combination of huperzine A and acetyl-L-carnitine in their range and concentration with the lower dose of the *Ginkgo biloba* at 120 mg interacts with the acetyl-L-carnitine and huperzine A and provides similar results and improvement for the factor derived "speed of attention" matter.

The *Ginkgo biloba* used in combination with the acetyl-L-carnitine and huperzine A may range from about 100 mg to about 160 mg in an example, and is 120 mg in a preferred composition. The composition in an example substitutes the *Ginkgo biloba* for the vinpocetine and maintains the acetyl-L-carnitine in an amount from about 1,160 mg to about 1,860 mg and the huperzine A in an amount from about 50 mcg to about 200 mcg. A preferred amount of acetyl-L-carnitine is about 1,395 mg and the huperzine A is about 150 mcg. These ranges of the three components of acetyl-L-carnitine, huperzine A and *Ginkgo biloba* are believed advantageous and work together even for a single dosage where the tasks involve briefly presented stimuli. A single dosage may be useful for short-term use to aid memory and cognition when the user is presented with rapidly presented material. The composition is also advantageous for long-term use over weeks, months and years.

Some published and reported studies involving the beneficial use of *Ginkgo biloba* have employed generally a minimum of about 120 to 240 mg/day or more of *Ginkgo biloba* over several months or years. Other similar studies have been found that an even larger dosage of *Ginkgo biloba* at 320 to 600 mg as a single dosage at one time enhances cognitive performance when a subject is presented briefly the stimuli, for example, large numbers of pictures or words. These studies have confirmed that even the single larger 320 to 600 mg dosage at one time aids in processing and recalling this information rapidly. The current composition with its reduced amount of *Ginkgo biloba*, e.g., a preferred 120 mg in one example, and using about 1,395 mg of acetyl-L-carnitine and 150 mcg of huperzine A is believed also to enhance a subject's cognitive performance when a subject is presented briefly stimuli such as large numbers of pictures or words. The composition at its ratios and concentration ranges for the huperzine A, acetyl-L-carnitine and *Ginkgo biloba* will aid in processing and recalling this information rapidly. However, the reduced amount of *Ginkgo biloba* at 120 mg as compared to the much higher 240 to 360 and higher milligram doses of *Ginkgo biloba* in the clinical trial results for enhanced speed of attention would not alone indicate such enhanced performance results are due to *Ginkgo biloba* alone. This benefit can be explained by the interaction among the other components as the acetyl-L-carnitine and huperzine A in their ratios and concentration ranges and are believed to be beneficial to allow this efficacy. These advantages may be attributed to the interaction of the huperzine A, *Ginkgo biloba* and acetyl-L-carnitine in the ratios and concentration ranges as described.

No adverse interactions are believed to occur when the huperzine A, *Ginkgo biloba*, and acetyl-L-carnitine are combined together and with other components that form the composition for either the Procera AVH, Ceretrophin and Procera XTF, including combination with other components such as *rhodiola*, biotin, alpha lipoic acid, green tea, and B vitamins, in an example. Using a reduced amount of the *Ginkgo biloba* such as 100 mg to about 160 mg, and at a preferred 120 mg, for example, in combination with the acetyl-L-carnitine and huperzine A with their ratios and concentration ranges is believed effective based on observation and work and believed as effective to improve not only performance in short-term memory tests and enhanced speed of attention as described above, but also effective with longer term use. In an example, the Ginkgo biloba used in the current composition is a leaf extract having 24% glycosides and 6% terpenes. The *Ginkgo biloba* could be a standard extract or it could be an extract specifically prepared for use with the acetyl-L-carnitine and the huperzine A and other added components.

Some commercially prepared preparations using Ginkgo biloba presented the *Ginkgo biloba* extract alone or in combination with Panex ginseng, e.g., as the composition commercially sold as Gincosan®. One reason for using Ginkgo biloba alone or in combination with Panex ginseng may result from a conventional belief that *Ginkgo biloba* interacts with many other drugs and herbs and has possible side effects and adverse interactions when combined with those drugs and/or herbal compositions, while also possibly losing its effectiveness. However, the inventor found that adverse interactions are minimal using the improved composition and components at these ratios and concentration ranges, for example, the *Ginkgo biloba*, huperzine A, acetyl-L-carnitine. These benefits exist even when other components are added as described below.

The following table illustrates two exemplary compositions that are advantageous when the *Ginkgo biloba* is substituted for vinpocetine and used in combination with acetyl-L-carnitine and huperzine A. Modified Formulation I corresponds to Procera AVH and the added components in Modified Formulation II correspond to Ceretrophin in these modified examples.

|  | Modified Formulation I | Modified Formulation II |
| --- | --- | --- |
| Acetyl-L-carnitine | 1,395 mg | 1,395 mg |
| *Ginkgo biloba* | 120 mg | 120 mg |
| Huperzine A | 150 mcg | 150 mcg |
| Alpha lipoic acid | —/— | 400 mg |
| Biotin | —/— | 500 mcg |
| *Rhodiola* | —/— | 300 mg |
|  | (Procera AVH) | (Ceretrophin) |

These composition examples may range in their ratios and concentration ranges as explained below. The acetyl-L-carnitine in one example is 83.90% active. The *Ginkgo biloba* in an example is 100% active, and may include 24% glycosides and 6% terpenes in a leaf extract as explained before. The huperzine A may be 1% active from *huperzine serrata*. Whole plant and aerial parts may be included as understood by those skilled in the art. Other components may include microcrystalline cellulose, silicon dioxide, stearic acid-vegetable sources and magnesium stearate vegetable. The composition may be contained within a vegetable cellulose capsule as one example of a delivery mechanism.

In the example of Modified Formulation I, the composition is formulated for oral administration such that the huperzine A, acetyl-L-carnitine and *Ginkgo biloba* together account for at least 80 weight percent of a dosage unit of the composition. The *Ginkgo biloba* in an example is about 5.0 percent to about 12.0 percent by weight of the huperzine A, acetyl-L-carnitine and *Ginkgo biloba*. In this example, the *Ginkgo biloba* and acetyl-L-carnitine are in a ratio of y:z respectively, wherein y is between about 690 and 1,030 for *Ginkgo biloba* and z is between about 8,000 and 12,000 for acetyl-L-carnitine.

In another example, the huperzine A, *Ginkgo biloba* and acetyl-L-carnitine are in a ratio of x:y:z, respectively, wherein x is between about 0.85 and about 1.3 for huperzine A, y is between about 690 and about 1,030 for *Ginkgo biloba*, and z is between about 8,000 and about 12,000 for acetyl-L-carnitine. In another example, x is between about 0.95 and about 1.20 for huperzine A, y is between about 775 and about 945 for Ginkgo biloba, and z is between about 9,000 and 11,000 for acetyl-L-carnitine.

These ratios may correspond in an example when the acetyl-carnitine is present in an amount from about 1,160 mg to about 1,860 mg, the *Ginkgo biloba* is present in the amount from about 100 mg to about 160 mg, and the huperzine A is present in an amount from about 50 mcg to about 200 mcg. In these examples, the term "about" can correspond to a plus or minus 10% value and the components of the composition will be within the desired ranges that make the composition efficacious for its intended purpose.

As with the compositions described above using vinpocetine, in this example, the modified composition having the huperzine A, *Ginkgo biloba* and acetyl-carnitine may together account for at least 90 weight percent of the dosage unit of the composition. In another example, the huperzine A, *Ginkgo biloba* and acetyl-L-carnitine may together account for at least 95 weight percent of the dosage unit of the composition. In different examples, the dosage unit of the composition may have a dosage unit equal to or less than 1,200 mg, or equal to or less than 1,500 mg or equal to or less than 1,600 mg, or equal to or less than 2,000 mg, or equal to or less than about 2,400 mg. In one proposed example, the dosage unit of the composition is equal to or less than about 1,500 mg and in another example, the composition dosage unit is about 1,515 mg corresponding to the example of Modified Formulation I.

Modified Formulation II is similar to Modified Formulation I and includes the additional components of biotin, alpha lipoic acid and *rhodiola*. Modified Formulation II may correspond in this example to Ceretrophin. The *rhodiola* is a preferred *rhodiola* extract that is standardized to 3% rosavins and 1% salidroside. Thus, in the example, the composition includes for Modified Formulation II the huperzine A; *rhodiola; Ginkgo biloba*; acetyl-L-carnitine, biotin; and alpha lipoic acid. In an example, the composition is formulated for oral administration such that the huperzine A, *rhodiola, Ginkgo biloba*, acetyl-L-carnitine, biotin and alpha lipoic acid together account for at least 80 weight percent of a dosage unit of the composition and the *Ginkgo biloba* is about 3.5% to about 8.5% by weight of the huperzine A, *rhodiola, Ginkgo biloba*, acetyl-L-carnitine, biotin and alpha lipoic acid. In an example, the alpha lipoic acid is about 11% to about 26% by weight of the huperzine A, *rhodiola, Ginkgo biloba*, acetyl-L-carnitine, biotin and alpha lipoic acid. The *Ginkgo biloba* and acetyl-L-carnitine are in a ratio of y:z respectively wherein the y is between about 690 and 1,030 for *Ginkgo biloba*, and z is between about 8,000 and 12,000 for acetyl-L-carnitine. In yet another example, when compared to the 8,000 to 12,000 for the acetyl-L-carnitine, the *rhodiola* may be between about 1,700 and 2,600 and the alpha lipoic acid may be between about 2,300 and 3,440. The biotin may be between about 2.85 and 4.3. In yet another example, the *rhodiola* may be between about 1,935 and 2,365.

These components may vary in their ratios and concentration ranges, and in an example, the acetyl-L-carnitine is present in an amount from about 1,160 mg to about 1,860 mg. The *rhodiola* is present in an amount from about 250 mg to about 350 mg. The huperzine A is present in an amount from about 50 mcg to about 200 mcg. The *Ginkgo biloba* is present in amount from about 100 mg to about 160 mg. The alpha lipoic acid is present in an amount from about 300 mg to about 500 mg. The biotin is present in an amount from about 400 mcg to about 600 mcg. In different examples, the dosage unit of the composition is equal to or less than about 1,200 mg, equal to or less than about 1,500 mg, and in a preferred example, the dosage unit is about 1,515 mg. In other examples, the dosage unit is equal to or less than about 1,600 mg, or equal to or less than about 2,000 mg, and in yet another example, equal to or less than about 2,400 mg.

Similar to previous formulations described above, the effective daily dosage may be administered between once daily and four times daily in dosage units of accordingly adjusted weight. Again the term "about" in conjunction with a numeral may refer to a range of that numeral as plus or minus 10% inclusive.

Other ingredients may be added such as folic acid, for example, at an example of about 0.1 mg per dosage unit, and in another example, at about 1 mg per dosage unit or a desired range therebetween. Potassium may be added such as at least about 10 mg per dosage unit. In yet another example, and more preferably, at least 100 mg of potassium may be added if it is used or in a range therebetween per dosage unit. The other inactive ingredients as noted before may be used. In an example as noted before, the daily dosage unit of the composition as a supplement is formulated to be about 1,200 mg, about 1,500 mg, about 2,000 mg or about 2,400 mg. Suitable oral single dosage forms may have a weight between about 200 mg and 600 mg as non-limiting examples. Regardless of the form, the different component ratios and ranges as described above preferably apply.

The beneficial interaction of the *Ginkgo biloba* with huperzine A and acetyl-L-carnitine may result from the chemical, physiological and/or functional aspects of the *Ginkgo biloba* and its various components functioning together with the combined huperzine A and acetyl-L-carnitine in the concentration ranges and ratios as described. Adverse effects are believed minimal and the inventor has found that the combination of Ginkgo biloba, acetyl-L-carnitine and huperzine A with their ratios and concentration ranges is advantageous. The new compositions as the Modified Formulations I and II using huperzine A, Ginkgo biloba and acetyl-L-carnitine (Modified Formulation I) and the added components (Modified Formulation II) have been found advantageous and believed to have minimal side effects, minimal negative interactions among each other, and a positive interaction with the benefits as described.

The *Ginkgo biloba* extract may be formed as a concentrate and obtained from its leaves whether dried or fresh and prepared in one example using an acetone-water solution. The *Ginkgo biloba* extract is known to have a number of flavonoids and many other natural plant products, many of them containing a series of carbon rings. For example, different flavonoids in the *Ginkgo biloba* extract may include isorhamnetin, D-glucaric acid, anacardic acid, and kaempterol-3. One positive advantage of combining the *Ginkgo biloba* and the huperzine A and acetyl-L-carnitine in the ratios and concentration ranges of the new composition is that the flavonoids may be better absorbed following ingestion. The half-lives usually are about 3 to 10 hours and any added absorption is beneficial. Bioflavonoids may include amentoflavone, ginkgetin, isoginketine, bilobetin, and terpenes such as diterpenes, for example, ginkgolide A, ginkgolide B, and ginkolide C and the sesquiterpene bilobalide. A standard Ginkgo biloba extract used for the composition could be EGb 761. As noted before, some studies using *Ginkgo biloba* alone have employed the generally higher concentration range of at least about a minimum of 120-240 mg/day and delivered over several months for longer term cognitive benefits. Other studies used higher ranges of 240, 320 or 600 mg as single dosages of Ginkgo biloba for short-term cognitive benefits, including enhancing speed of attention factors. Those studies using these acute doses at higher concentrations appeared to benefit the users for rapid information processing and performance, especially on briefly presented information, and the subjects appeared to show better recall of rapidly presented material immediately after the material is presented. One study had subjects taking the *Ginkgo biloba* extract EGb 761 at higher acute dosages of 320 mg or 600 mg and studied a battery of tests given to those subjects. The test results showed an improved performance in the Sternberg short-term memory test for an improvement in the speed of information processing. Another example is the trial reported in Allain et al., "Effects of Two Doses of *Ginkgo Biloba* Extract (EGb 761) on the Dual-Coding Test in Elderly Subjects," *Clin Ther,* 1993 May-June; 15(3):549-58. The inventor has surprisingly observed, however, that the lower amount of 120 mg as a dosage unit and at a preferred range of about 100 mg to about 160 mg of the *Ginkgo biloba* extract in combination with the huperzine A and acetyl-L-carnitine and substituting for the vinpocetine as used in the clinical trials above is efficacious. It also appeared as if higher dosages of *Ginkgo biloba* had been used and observed that subjects do well on a battery of tests, including the short term tests.

There may be many plausible reasons for the efficacy of the Modified Formulations using *Ginkgo biloba*. It is known that the *Ginkgo biloba* extract may stimulate vasodilation and increase cerebral blood flow and lower blood pressure. Plausible reasons exist for the beneficial interaction among the reduced amount of *Ginkgo biloba* with the acetyl-L-carnitine and the huperzine A in the ratios and concentration ranges as described. However, it should also be understood that the ginkgolide B terpene is a potent antagonist against platelet activity factor and inhibits platelet aggregation, fibrinolysis, and thrombin activity and for that reason, care is often given when employing the *Ginkgo biloba* extract, especially in combination with other components. The interaction of the reduced amount of *Ginkgo biloba* with the other components makes up for not having a higher concentration such as for enhancing speed of memory. The new composition may have excellent antioxidant properties and may help inhibit or alleviate cell damage caused by free oxygen radicals to the aging process that could also be associated with the neuropathology underlying Alzheimer's Disease. The *Ginkgo biloba* extract and its combination with acetyl-L-carnitine and huperzine A may inhibit the activity of the superoxide dismutase and monoamine oxidase as enzymes that may produce free radicals in the brain and body. The *Ginkgo biloba* extract in combination with huperzine A and acetyl-L-carnitine may also help scavenge free radicals.

It is also possible the composition may protect neurons from oxidative stress, e.g., apoptosis and also reduce the toxic effects of cerebral ischemia. The composition may also reduce the production of arachidonic acid as a toxic by-product of lipid metabolism. The diterpenes and sesquiterpenes may protect brain tissue against brain injury caused by reduced oxygen or blood flow and work in conjunction with the acetyl-L-carnitine and huperzine A. Even if the flavonoids and bioflavonoids may not pass through the blood-brain barrier easily, their effect with the composition as described may still have antioxidant action. By selecting a particular type of *Ginkgo biloba* extract and/or its processing and preparation, it is possible to manipulate the amount of ginkgolide B and bilobalide and their components to provide neuroprotective and anti-apoptotic effects.

The composition as the described combination of components may have a positive impact on the forebrain's acetylcholine system and the acetylcholine neurons that absorb choline from the body. Energy-dependent transport processes may be enhanced, for example, by increasing the amount of acetylcholine that is produced. The composition may possibly increase the glucose use in the frontal and parietal cortex and enhance glucose utilization in the nucleus accumbens and cerebellum. The composition may also have an indirect action on the neurotransmitter serotonin and act upon the 5HT-1A serotonin receptor. The composition may possibly reduce stress-induced elevation of glucocorticoid levels. The composition may also enhance release of the neurotransmitter, GABA or gamma-amino butyric acid.

Other components in the *Ginkgo biloba* may also be advantageous when combined in the concentration ranges and ratios with the huperzine A and acetyl-L-carnitine and optionally the other components as described above. For example, the flavonol and flavone glycosides, lactone derivatives such as the ginkolides, the bilide, ascorbic acid, catechin, iron-basic superoxides, 6-hydroxykinuretic acid, protocatechuic acid, shikimic acid, sterols, and vanilic acid may work individually or selectively together. Care is preferably taken when forming the extract so that a minimal amount of the ginkgotoxin (4-O-methoxypyridoxine) is produced. There also may be some synergistic interaction among the *Ginkgo biloba*, huperzine A and acetyl-L-carnitine to improve blood flow throughout the body and restore some balance between prostacyclin and thromboxane A2 to improve vessel regulation. The composition may inhibit monoamine oxidase A and B and inhibit the catechol-O-methyl transferase as an enzyme that breaks down adrenergic transmitters while increasing the number of alpha-adrenoreceptors in the brain since those alpha-adrenoreceptors decrease with age. There may be some effect on benzodiazepine receptors and a decrease in glucocorticoid biosynthesis and increased pancreatic beta-cell function with glucose loading. The cyanogenic glycosides may have some antibacterial and antifungal effects.

Even though it is shown by clinical trials that the larger dosages of *Ginkgo biloba* between 300 and 600 mg enhance speed of attention and benefit short term memory in these larger dosages may cause some restlessness, diarrhea, nausea, vomiting and weakness. The lower dosage of *Ginkgo biloba* of about 100 to 160 mg in combination with huperzine A and acetyl-L-carnitine and in the specific concentration ranges and ratios is advantageous and believed does not produce the above mentioned adverse effects. There may be further reasons supporting benefits.

The amino acid L-carnitine is known to be produced by the liver and kidneys and transported to the brain and heart. In an example, it is formed from the amino acids lysine and methionine, but the acetyl-L-carnitine is more advantageous because it crosses the blood-brain barrier. In combination with *Ginkgo biloba* and huperzine A, the composition may increase energy production in the mitochondria and boost not only mental energy, but also physical energy, while increasing the neurotransmitters serotonin and norepinephrine. The acetyl-L-carnitine has anti-inflammatory and antioxidant properties to protect brain cells from free radical damage and protect them from toxins and oxygen deprivation. It is well known that the aging process affects the energy producing capabilities of mitochondria. The new composition may help alleviate the accumulation of cellular debris and transport fatty acids from the cytosol into the mitochondria within the cell where fats are oxidized to produce ATP. Acetyl-L-carnitine is the acetylated ester of the amino acid L-carnitine and is an endogenous mitochondrial membrane to help maintain the mitochondrial biochemical energetics and lower the increased oxidative stress that results from aging. The acetyl-L-carnitine may operate with the *Ginkgo biloba* and huperzine A and aid in carrying long-chain fatty acids across the membrane into the mitochondria and across the blood-brain barrier. It may aid in treating or possibly preventing excess oxidative damage. Some acetyl-L-carnitine supplements employed in trials used the larger amounts at around 1.5 to 3.0 grams a day dose. The inventor has found that the reduced amount of the acetyl-L-carnitine in combination with the huperzine A and *Ginkgo biloba* is beneficial.

Huperzine A may also operate in combination with the *Ginkgo biloba* and acetyl-L-carnitine as a brain booster to raise acetylcholine levels even higher than when acting alone. The composition may increase the neurotransmitter acetylcholine by blocking the enzyme that breaks it down and promotes new brain cell generation while protecting against some environmental toxins while operating as an antioxidant. The combination of huperzine A may target acetylcholinesterase to prevent the break down of acetylcholine within the synaptic cleft to increase the acetylcholine levels.

The composition also is advantageous and uses a reduced amount of biotin at a preferred 0.5 mg, as compared to some commercial daily doses of biotin that range from 1.8 mg to 5.0 mg, amounts that were also employed in some biotin trials. Additionally, the composition includes a reduced amount of alpha lipoic acid such as the preferred 400 mg as compared to some commercially available 600 to 900 mg amounts used in supplements. The chemical structure of biotin is similar to that of alpha lipoic acid and the reduced concentration ranges in the new composition are below what is normally used commercially for those components. The reduced amounts in the new composition have less tendency to compete with each other and interfere with their activity in the body, especially since greater amounts of alpha lipoic acid may compete with greater amounts of biotin and interfere with its activity in the body.

The alpha lipoic acid works in conjunction with the biotin and helps recycle vitamins E and C to be used again. The alpha lipoic acid improves cognitive function and is believed to improve memory-related signaling pathways, reduce oxidative stress, and restore the activity of acetylcholinesterase and NA+, K+-ATPpase. The alpha lipoic acid may be provided in different forms, such as the alpha R-lipoic acid, alpha S-lipoic acid, and alpha RS-lipoic acid where the alpha S-lipoic acid and alpha RS-lipoic acid are synthetic, while the alpha R-lipoic acid is found in nature. The R-lipoic acid contains only the natural (CIS) form a lipoic acid and even greater reduced amounts may be used. When the synthetic (trans) form of the alpha lipoic acid is used, a larger amount such as a preferred 400 mg is used.

The huperzine A is also at a reduced amount such as 0.15 mg (150 mcg) as compared to other commercial examples and amounts used in cognitive testing where a higher 400 mcg of a daily dose was employed.

The Procera XTF extreme focus composition includes the basic Procera AVH with its huperzine A, *Ginkgo biloba* and acetyl-L-carnitine as the ingredients, plus additional performance-boasting and stress-fighting ingredients that include *rhodiola* rosea, a B vitamin complex as vitamins B3, B5 and B6 that are often depleted by exhausting mental challenges or stress and green tea and guarana extract. This composition is advantageous for those higher pressure moments when an extra mental boost is required. This composition includes the Procera AVH components of the huperzine A, *Ginkgo biloba* and acetyl-L-carnitine and the added components. The *Ginkgo biloba*, *rhodiola* and acetyl-L-carnitine are in a ratio a:b:c respectively and in an example such that a as the *Ginkgo biloba* is between about 690 and 1,030, b as the *rhodiola* is between about 1,700 and 2,600, and c as the acetyl-L-carnitine is between about 8,000 and 12,000. This composition is formulated for oral administration such that the *Gingko biloba*, *rhodiola*, acetyl-L-carnitine and huperzine A together account for at least 80 wt % of a dosage unit of the nutritional supplement composition. The huperzine A (d) is in a ratio a:b:c:d with the *Ginkgo biloba*, *rhodiola*, and acetyl-L-carnitine, and huperzine A is between about 0.85 and 1.3 in an example. The vitamin B complex (e) may be in a ratio a:b:c:e with the *Ginkgo biloba*, *rhodiola* and acetyl-L-carnitine such that e as the vitamin B complex is between 860 and 1,290.

As noted before, the vitamin B complex comprises vitamins B3, B5 and B6, and in an example, the vitamin B3 comprises niacin and niacinamide and the vitamin B5 comprises pantothenic acid as D-calcium pantothenate. The Procera XTF composition also may include a green tea and guarana extract (f) in a ratio a:b:c:f with the *Gingko biloba*, *rhodiola*, and acetyl-L-carnitine such that f as the green tea and guarana extract between about 1,700 and 2,600. It is also possible that the *Ginkgo biloba*, *rhodiola*, acetyl-L-carnitine and huperzine A are in a weight ratio to each other such that the *Ginkgo biloba* is between about 775 and 945, the *rhodiola* is between about 1,935 and 2,365, the acetyl-L-carnitine is between about 9,000 and 11,000, and the huperzine A is between about 0.95 and 1.2. Each of the vitamins B3, B5 and B6 may be between about 290 to 430.

In an example, the acetyl-L-carnitine is present in an amount from about 1,160 mg to about 1,860 mg and preferably about 1,395 mg. The *Ginkgo biloba* is present in amount from about 100 mg to about 160 mg and preferably about 120 mg. Its lower range could be 80 mg in some examples. *Rhodiola* is present in an amount from about 250 mg to about 350 mg and preferably about 300 mg. It could range in some cases from about 200 to 400 mg. The huperzine A is present in an amount from about 50 mcg to about 200 mcg and preferably about 150 mcg. Its upper range could be close to 250 mcg in some examples. The green tea and guarana extract is present in an amount from about 250 mg to about 350 mg and preferably about 300 mg. In an example, the vitamin B complex is present in an amount from about 125 mg to about 175 mg, and each of the vitamins B3, B5 and B6 is present in an amount from about 40 mg to about 60 mg and preferably about 50 mg each. In some instances, these concentrations per daily dose could be provided in four capsules daily. It is also possible that these amounts could be halved and two capsules taken daily. The ratios remain the same, but the concentration ranges would be halved. This may be advantageous for those who are less amenable in comfort to the full composition and have minor problems such as stomach or other ailments.

As noted before, the *rhodiola* comprises about 2% to about 4% rosavins and 0.5% to 1.5% salidrosides. The composition may be formulated with an enteric coating. Inactive ingredients may be included such as a carrier, a binder, an excipient, a dye, and combinations of those components.

The B vitamin complex offers advantages. For example, vitamin B3 includes niacin that may up regulate brain-derived neurotrophic factor (BDNF) and tropomyosin receptor kinase B (TrkB) expression. Vitamin B3 has a number of anti-inflammatory effects in different tissues such as the brain and vascular tissue through the activation of NIACR1. This may attenuate neuro-inflammation and have efficacy in treating the neuro immune disorders, including multiple sclerosis and Parkinson's disease. It may also activate the G protein-coupled estrogen receptor (GPER).

Vitamin B5 as pantothenic acid may increase the effect of other components of the composition as the cholinesterase inhibitors. There could be some synergy between the different components in this regard. The vitamin B5 as pantothenic acid may also synthesize coenzyme-A (coA) and synthesize and metabolize proteins, carbohydrates and fats.

Vitamin B6 is also known as pyridoxine and aids in allowing the body to make different neurotransmitters and aids in normal brain development and function while also helping the body make the hormones serotonin and norepinephrine to influence mood. It may also help make melatonin in the body. The serotonin and norepinephrine aid in transmitting signals to the brain. Vitamin B6 may also aid in forming myelin as a protein layer around nerve cells. Some of the other components in the composition may also aid the active form as pyridoxal 5'-phosphate (PLP) that serves as a coenzyme for different enzyme reactions in amino acid, glucose and lipid metabolism.

The B vitamins may work also in conjunction with the green tea and guarana extract. Green tea may have a thermogenic effect and with the guarana includes catechin and epigallocatechin-3-gallate (EGCG) to aid in energy expenditure, substrate oxidation and help lower blood pressure. It also may aid in reducing the vasoconstrictive effects of caffeine on the brain. The green tea includes the different phytochemicals such as the polyphenols in caffeine.

The green tea extract may operate as an antioxidant and as with the similar family grape seed and pine bark extracts, includes polyphenols and flavonoids such as proanthocyanidins. The main proanthocyanidins include catechins, e.g., epigallocatechin gallate (ECGG), as noted above for example, and as found in green tea. The extract may operate as a natural telomerase inhibitor and may regulate blood sugar, reduce triglycerides, and possibly reverse heart disease. It may aid to prevent DNA damage, aid brain health, and serve as an effective monoamine oxidase (MAO) inhibitor.

Thus, specific embodiments of nutritional supplements for enhancing cognitive function have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

This application is related to copending patent applications entitled, "COMPOSITIONS AND METHODS FOR ENHANCING BRAIN FUNCTION USING ACETYL-L-CARNITINE, HUPERZINE A, *GINKGO BILOBA*, AND VITAMIN B COMPLEX," which is filed on the same date and by the same assignee and inventors, the disclosure which is hereby incorporated by reference.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed:

1. A nutritional supplement composition for enhancing cognitive function, comprising:
   huperzine A;
   Ginkgo biloba; and
   acetyl-L-carnitine;
   wherein the composition is formulated for oral administration such that huperzine A, acetyl-L-carnitine, and Ginkgo biloba together account for at least 80 wt % of a dosage unit of the composition and the Ginkgo biloba is about 5.0% to about 12.0% by weight of the huperzine A, acetyl-L-carnitine and Ginkgo biloba, and the Ginkgo biloba and acetyl-L-carnitine are in a ratio of y:z respectively, wherein y is between about 690 and 1,030 for Ginkgo biloba and z is between about 8,000 and 12,000 for acetyl-L-carnitine.

2. The nutritional supplement composition of claim 1, wherein the huperzine A, Ginkgo biloba, and acetyl-L-carnitine are in a ratio of x:y:z, respectively, wherein x is between about 0.85 and about 1.3 for huperzine A, y is between about 690 and about 1,030 for Ginkgo biloba, and z is between about 8,000 and about 12,000 for acetyl-L-carnitine.

3. The nutritional supplement composition of claim 2, wherein x is between about 0.95 and about 1.20 for huperzine A, y is between about 775 and about 945 for Ginkgo biloba, and z is between about 9,000 and about 11,000 for acetyl-L-carnitine.

4. The nutritional supplement composition of claim 1, wherein acetyl-L-carnitine is present in an amount from about 1,160 mg to about 1,860 mg.

5. The nutritional supplement composition of claim 1, wherein Ginkgo biloba is present in an amount from about 100 mg to about 160 mg.

6. The nutritional supplement composition of claim 1, wherein huperzine A is present in an amount from about 50 mcg to about 200 mcg.

7. The nutritional supplement composition of claim 1, wherein the composition is formulated with an enteric coating.

8. The nutritional supplement composition of claim 1, further comprising an inactive ingredient selected from the group consisting of a carrier, a binder, an excipient, a dye, and combinations thereof.

9. The nutritional supplement composition of claim 1, wherein huperzine A, Ginkgo biloba, and acetyl-L-carnitine together account for at least 90 wt % of a dosage unit of the composition.

10. The nutritional supplement composition of claim 1, wherein huperzine A, Ginkgo biloba, and acetyl-L-carnitine together account for at least 95 wt % of the dosage unit of the composition.

11. The nutritional supplement composition of claim 1, wherein the dosage unit of the composition is equal to or less than about 1,500 mg.

12. A nutritional supplement composition for enhancing cognitive function, comprising:
huperzine A;
rhodiola;
Ginkgo biloba;
acetyl-L-carnitine;
biotin; and
alpha lipoic acid;
wherein the composition is formulated for oral administration such that the huperzine A, rhodiola, Ginkgo biloba, acetyl-L-carnitine, biotin, and alpha lipoic acid together account for at least 80 wt % of a dosage unit of the composition and the Ginkgo biloba is about 3.5 percent to about 8.5 percent by weight of the huperzine A, rhodiola, Ginkgo biloba, acetyl-L-carnitine, biotin and alpha lipoic acid and the alpha lipoic acid is about 11.0 percent to about 26.0 percent by weight of the huperzine A, rhodiola, Ginkgo biloba, acetyl-L-carnitine biotin and alpha lipoic acid, and the Ginkgo biloba and acetyl-L-carnitine are in a ratio of y:z respectively, wherein y is between about 690 and 1,030 for Ginkgo biloba, and z is between about 8,000 and 12,000 for acetyl-L-carnitine.

13. The nutritional supplement composition of claim 12, wherein acetyl-L-carnitine is present in an amount from about 1,160 mg to about 1,860 mg.

14. The nutritional supplement composition of claim 12, wherein rhodiola is present in an amount from about 250 mg to about 350 mg.

15. The nutritional supplement composition of claim 12, wherein huperzine A is present in an amount from about 50 mcg to about 200 mcg.

16. The nutritional supplement composition of claim 12, wherein Ginkgo biloba is present in an amount from about 100 mg to about 160 mg.

17. The nutritional supplement composition of claim 12, further wherein alpha lipoic acid is present in an amount from about 300 mg to about 500 mg.

18. The nutritional supplement composition of claim 12, wherein biotin is present in an amount from about 400 mcg to about 600 mcg.

19. The nutritional supplement composition of claim 12, wherein the dosage unit of the composition is equal or less than about 1,500 mg.

20. A nutritional supplement composition for enhancing cognitive function, comprising:
huperzine A;
Ginkgo biloba; and
acetyl-L-carnitine;
wherein the composition is formulated for oral administration such that huperzine A, acetyl-L-carnitine, and Ginkgo biloba together account for at least 80 wt % of a dosage unit of the composition and the Ginkgo biloba is about 5.0% to about 12.0% by weight of the huperzine A, acetyl-L-carnitine and Ginkgo biloba, and wherein the Ginkgo biloba is present in an amount from about 100 mg to about 160 mg, and wherein the Ginkgo biloba and acetyl-L-carnitine are in a ratio of y:z respectively, wherein y is between about 690 and 1,030 for Ginkgo biloba and z is between about 8,000 and 12,000 for acetyl-L-carnitine.

21. The nutritional supplement composition of claim 20, wherein the huperzine A, Ginkgo biloba, and acetyl-L-carnitine are in a ratio of x:y:z, respectively, wherein x is between about 0.85 and about 1.3 for huperzine A, y is between about 690 and about 1,030 for Ginkgo biloba, and z is between about 8,000 and about 12,000 for acetyl-L-carnitine.

22. The nutritional supplement composition of claim 20, wherein x is between about 0.95 and about 1.20 for huperzine A, y is between about 775 and about 945 for Ginkgo biloba, and z is between about 9,000 and about 11,000 for acetyl-L-carnitine.

23. The nutritional supplement composition of claim 20, wherein the composition is formulated with an enteric coating.

24. The nutritional supplement composition of claim 20, further comprising an inactive ingredient selected from the group consisting of a carrier, a binder, an excipient, a dye, and combinations thereof.

25. The nutritional supplement composition of claim 20, wherein huperzine A, Ginkgo biloba, and acetyl-L-carnitine together account for at least 95 wt % of the dosage unit of the composition.

26. The nutritional supplement composition of claim 20, wherein the dosage unit of the composition is equal to or less than about 1,600 mg.

* * * * *